United States Patent
Rao et al.

(10) Patent No.: US 10,344,165 B2
(45) Date of Patent: Jul. 9, 2019

(54) 2,7-DISUBSTITUTED CEPHALOSPORIN DERIVATIVES AS β-LACTAMASE SUBSTRATES AND METHODS FOR THEIR USE FOR THE DIAGNOSIS OF TUBERCULOSIS

(71) Applicants: The Texas A&M University System, College Station, TX (US); The Board of Trustees of the Leland Stanford Junior University, Palo Alto, CA (US)

(72) Inventors: Jianghong Rao, Sunnyvale, CA (US); Hexin Xie, Mountain View, CA (US); Yunfeng Cheng, Palo Alto, CA (US); Jeffrey D. Cirillo, College Station, TX (US)

(73) Assignees: The Texas A&M University System, College Station, TX (US); The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 15/831,266

(22) Filed: Dec. 4, 2017

(65) Prior Publication Data
US 2018/0094139 A1    Apr. 5, 2018

Related U.S. Application Data

(62) Division of application No. 14/613,214, filed on Feb. 3, 2015, now Pat. No. 9,834,681.

(60) Provisional application No. 61/935,712, filed on Feb. 4, 2014.

(51) Int. Cl.

| | | |
|---|---|---|
| *C07D 501/52* | (2006.01) | |
| *C09B 11/24* | (2006.01) | |
| *C09B 57/02* | (2006.01) | |
| *C07D 501/62* | (2006.01) | |
| *C12Q 1/04* | (2006.01) | |
| *C12Q 1/18* | (2006.01) | |
| *C12Q 1/34* | (2006.01) | |

(52) U.S. Cl.
CPC ............ *C09B 11/24* (2013.01); *C07D 501/52* (2013.01); *C07D 501/62* (2013.01); *C09B 57/02* (2013.01); *C12Q 1/04* (2013.01); *C12Q 1/18* (2013.01); *C12Q 1/34* (2013.01); *G01N 2333/30* (2013.01); *G01N 2333/986* (2013.01); *G01N 2800/12* (2013.01); *G01N 2800/52* (2013.01)

(58) Field of Classification Search
CPC .............................. C07D 501/52; C07D 501/62
USPC .......................................................... 540/217
See application file for complete search history.

(56) References Cited

U.S. PATENT DOCUMENTS

| | | | | |
|---|---|---|---|---|
| 3,843,640 | A | * | 10/1974 | Spry ................... C07D 501/04 540/228 |
| 8,318,450 | B2 | | 11/2012 | Corry et al. |
| 2009/0246862 | A1 | | 10/2009 | Rao et al. |
| 2010/0261700 | A1 | | 10/2010 | Sutton |

FOREIGN PATENT DOCUMENTS

| | | |
|---|---|---|
| WO | 2005/071096 A2 | 8/2005 |
| WO | 2006/085978 A2 | 8/2006 |
| WO | 2013/173519 A1 | 11/2013 |

OTHER PUBLICATIONS

Communication Pursuant to Article 94(3) EPC dated Apr. 12, 2018, issued in European Application No. 15 746 117.9, filed Feb. 3, 2015, 5 pages.
Cheng, Y., et al., "Fluorogenic Probes With Substitutions at the 2 and 7 Positions of Cephalosporin Are Highly BlaC-Specific for Rapid *Mycobacterium tuberculosis* Detection," Angewandte Communications International Edition 53(35):9360-9364, Jul. 2014.
Communication Pursuant to Rules 70(2) and 70a(2) EPC dated Sep. 12, 2017, issued in European Application No. 15746117.9, filed Feb. 3, 2015, 1 page.
Extended European Search Report dated Aug. 25, 2017, issued in European Application No. 15746117.9, filed Feb. 3, 2015, 8 pages.
Xie, H., et al., "Rapid Point-of-Care Detection of the Tuberculosis Pathogen Using a BlaC-Specific Fluorogenic Probe," Nature Chemistry 4(10):802-809, Oct. 2012.
International Search Report and Written Opinion dated Jul. 9, 2015, issued in corresponding International Application No. PCT/US2015/014295, filed Feb. 3, 2015, 12 pages.

* cited by examiner

*Primary Examiner* — Kahsay Habte
(74) *Attorney, Agent, or Firm* — Christensen O'Connor Johnson Kindness PLLC

(57) ABSTRACT

β-Lactamase substrates and methods for using the substrates to detect β-lactamase and to diagnose tuberculosis.

19 Claims, 21 Drawing Sheets

| Name | BlaC | | | TEM-1 Bla | | | Penicillinase from *Bacillus cereus* | | | Spontaneous Hydrolysis Rate |
|---|---|---|---|---|---|---|---|---|---|---|
| | $K_m$ (μM) | $k_{cat}$ (s$^{-1}$) | $k_{cat}/K_m$ (s$^{-1}$M$^{-1}$) | $K_m$ (μM) | $k_{cat}$ (s$^{-1}$) | $k_{cat}/K_m$ (s$^{-1}$M$^{-1}$) | $K_m$ (μM) | $k_{cat}$ (s$^{-1}$) | $k_{cat}/K_m$ (s$^{-1}$M$^{-1}$) | (x 10$^{-7}$ s$^{-1}$) |
| CDC-1 | 63 ± 6$^b$ | 13 ± 0.5$^b$ | 2.1 x 10$^{5,b}$ | 135 ± 16$^b$ | 48 ± 3.8$^b$ | 3.6 x 10$^{5,b}$ | ND | ND | ND | 2.4$^b$ |
| 2R-CDC-1 | 13.0 ± 1.0 | 1.5 ± 0.02 | 1.1 x 10$^5$ | 20.0 ± 0.04 | 5.5 ± 0.03 | 2.7 x 10$^5$ | ND | ND | ND | 5.1 |
| 2S-CDC-1 | 49.0 ± 2.9 | 5.9 ± 0.2 | 1.2 x 10$^5$ | 139.5 ± 12.3 | 5.6 ± 0.3 | 4.0 x 10$^4$ | ND | ND | ND | 2.9 |
| CDC-Cp | 13.9 ± 0.7 | 2.6 ± 0.03 | 1.9 x 10$^5$ | 69.5 ± 7.9 | 1.5 ± 0.1 | 2.2 x 10$^4$ | ND | ND | ND | 4.5 |
| CDC-OMe-Cp | 217.9 ± 13.3 | 9.5 ± 0.4 | 4.4 x 10$^4$ | 75.2 ± 17.5 | 5.2 ± 0.5 x 10$^{-5}$ | 0.7 | ND | ND | ND | 2.5 |
| CDG-1 | 2 ± 0.4$^b$ | 1 ± 0.1$^b$ | 5 x 10$^{5,b}$ | 2 ± 0.2$^b$ | 5 ± 0.1$^b$ | 2.5 x 10$^{6,b}$ | ND | ND | ND | 6$^b$ |
| CDG-OMe | 5 ± 0.3$^b$ | 0.8 ± 0.01$^b$ | 1.6 x 10$^{5,b}$ | 40 ± 4$^b$ | 7 ± 0.6 x 10$^{-4,b}$ | 18$^b$ | 10.9 ± 4 | 4.6 ± 0.9 x 10$^{-5}$ | 4.3 | 1.9$^b$ |
| CDG-3 | 4.6 ± 0.5 | 1.1 ± 0.03 | 2.4 x 10$^5$ | 3.5 ± 0.4 | 7.0 ± 0.2 x 10$^{-6}$ | 2 | 12.2 ± 5.5 | 3.1 ± 0.6 x 10$^{-6}$ | 0.3 | 1.0 |

*Fig. 2.*

2,7-DISUBSTITUTED CEPHALOSPORIN DERIVATIVES AS β-LACTAMASE SUBSTRATES AND METHODS FOR THEIR USE FOR THE DIAGNOSIS OF TUBERCULOSIS

CROSS-REFERENCE TO RELATED APPLICATIONS

This application is a division of U.S. application Ser. No. 14/613,214, filed Feb. 3, 2015, which claims the benefit of U.S. Provisional Application No. 61/935,712, filed Feb. 4, 2014, each expressly incorporated herein by reference in its entirety.

FIELD OF THE INVENTION

The present invention relates to β-lactamase substrates that are useful for the diagnosis of tuberculosis. Certain of the β-lactamase substrates are 2,7-disubstituted cephalosporin derivatives.

BACKGROUND OF THE INVENTION

Tuberculosis (TB) is a highly infectious airborne disease caused by the widely spread pathogen *Mycobacterium tuberculosis* (Mtb), infecting around one-third of the world's population and claiming the lives of 1.5 million each year. The worldwide emergence of multidrug-resistance tuberculosis (MDR-TB), extensively drug-resistant tuberculosis (XDR-TB), and totally drug-resistant tuberculosis (TDR-TB) further worsens this global health crisis. An important step in containing the spread of this deadly airborne disease is rapid, timely detection and diagnosis of Mtb, preferably at point-of-care (POC). However, the extremely slow growth rate of the virulent Mtb pathogen remains the largest hurdle to overcome. As a direct consequence, the gold standard culture-based technique for TB diagnosis is limited to patients with advanced infection and usually takes several weeks to produce a definitive diagnosis. Although nucleic acid-based diagnostic methods such as GeneXpert provide sensitive and specific diagnosis, the cost and requirement of highly skilled technical personnel and sophisticated instrument recalibration makes them less accessible in developing countries, where TB prevalence is highest.

One approach takes advantage of an enzyme expressed by Mtb, BlaC, as the biomarker for Mtb detection. BlaC is an Ambler class A β-lactamase that efficiently hydrolyzes β-lactam antibiotics and is central to the biochemical mechanism responsible for pervasive β-lactam-antibiotic resistance. Because the first β-lactamase was discovered in 1940, a large number of β-lactamases have been identified that can hydrolyze a variety of β-lactam antibiotics, from original penicillins, to cephalosporins, to the latest carbapenems. To assay the activity of β-lactamases, fluorogenic and luminogenic probes have been developed to take advantage of the high sensitivity of fluorescence and luminescence detection methods. However, most of these probes do not possess specificity for BlaC, and are broadly hydrolyzed by many β-lactamases, such as the common TEM-1 β-lactamase (TEM-1 Bla) in Gram-negative bacteria. Therefore, they are not suitable for Mtb diagnosis, because clinical materials can carry many other bacterial species that often express β-lactamases.

Despite the advances in the development of fluorescent probes for the detection of β-lactamase and the diagnosis of tuberculosis, a need exists for novel probes that facilitate the rapid detection of tuberculosis. The present invention seeks to fulfill this need and provides further related advantages.

SUMMARY OF THE INVENTION

The present invention provides β-lactamase substrates and methods and systems for using the substrates to detect β-lactamase.

In one aspect of the invention, β-lactamase substrates are provided. In one embodiment, the β-lactamase substrate is a compound having the formula:

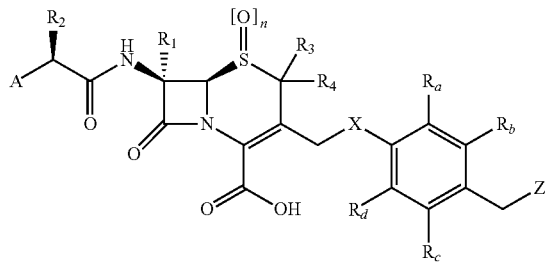

or an ester or a salt thereof,
wherein
A is selected from the group consisting of:
(a) substituted and unsubstituted C6-C10 aryl, and
(b) substituted and unsubstituted C3-C7 heteroaryl;
$R_1$ is selected from the group consisting of:
(a) hydrogen,
(b) methoxy, and
(c) ethoxy;
$R_2$ is selected from the group consisting of hydrogen, C1-C3 alkyl, C1-C3 alkyl substituted with one or more halogens, and substituted piperazine;
$R_3$ and $R_4$ are independently selected from the group consisting of hydrogen, methyl, ethyl, propyl, halomethyl, haloethyl, halopropyl, or $R_3$ and $R_4$ taken together with the carbon atom to which they are attached form a cyclopropyl or a cyclobutyl ring, provided that $R_3$ and $R_4$ are not both hydrogen;
n is 0 or 1;
$R_a$, $R_b$, $R_c$, and $R_d$ are independently selected from the group consisting of hydrogen, halogen, nitro, C1-C3 alkyl, and C1-C3 alkyl substituted with one or more halogens; and
Z is a reporting group that provides an optical signal when released from the compound.

In another embodiment, the invention provides a compound having the formula:

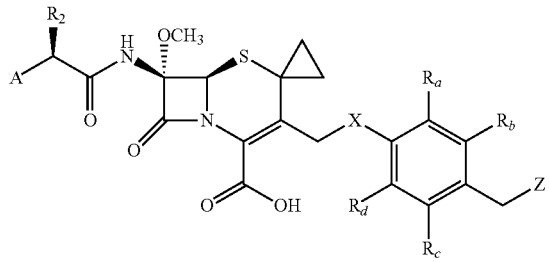

or an ester or a salt thereof.
In a further embodiment, the invention provides a compound having the formula:

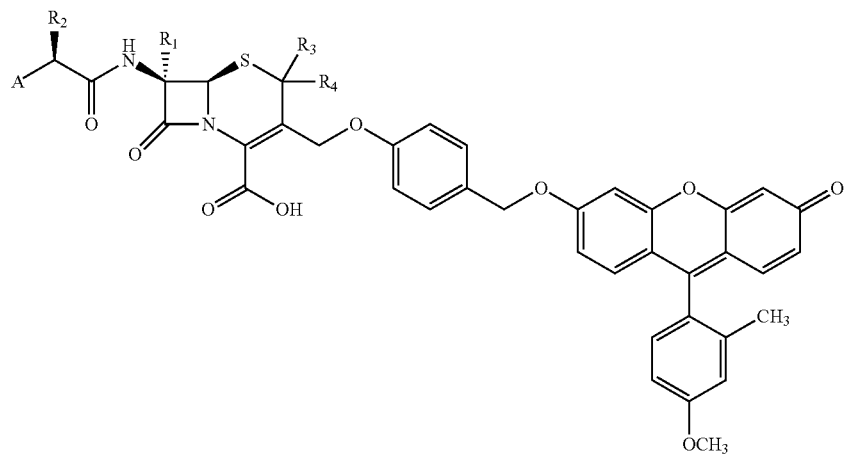

or an ester or a salt thereof.

In yet a further embodiment, the invention provides a compound having the formula:

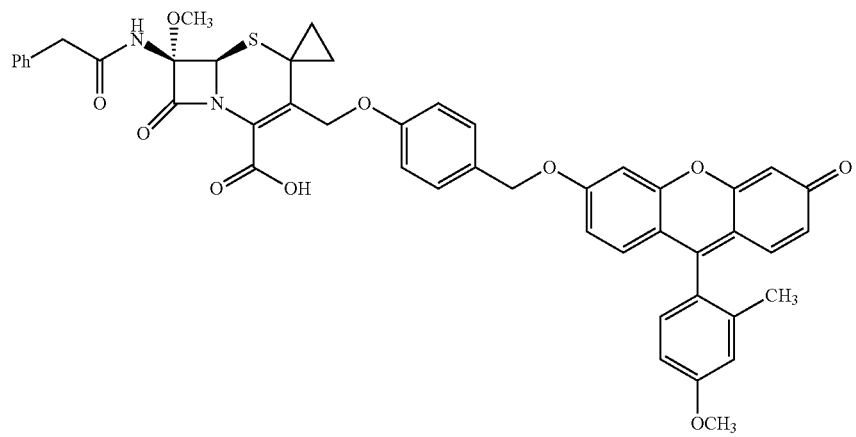 [SMILES: COc1ccc(-c2c3ccc(=O)cc-3oc3cc(OCc4ccc(OCC5=C(C(=O)O)N6C(=O)[C@](NC(=O)Cc7ccccc7)(OC)[C@H]6SC56CC6)cc4)ccc23)c(C)c1]

or an ester or a salt thereof.

In one embodiment, the invention provides a compound having the formula:

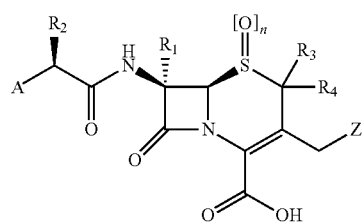

or an ester or a salt thereof,
wherein
A is selected from the group consisting of:
(a) substituted and unsubstituted C6-C10 aryl, and
(b) substituted and unsubstituted C3-C7 heteroaryl;
$R_1$ is selected from the group consisting of:
(a) hydrogen,
(b) methoxy, and
(c) ethoxy;

$R_2$ is selected from the group consisting of hydrogen, C1-C3 alkyl, C1-C3 alkyl substituted with one or more halogens, and substituted piperazine;

$R_3$ and $R_4$ are independently selected from the group consisting of hydrogen, methyl, ethyl, propyl, halomethyl, haloethyl, halopropyl, or $R_3$ and $R_4$ taken together with the carbon atom to which they are attached form a cyclopropyl or a cyclobutyl ring, provided that $R_3$ and $R_4$ are not both hydrogen;

n is 0 or 1; and

Z is a reporting group that provides an optical signal when released from the compound.

In another embodiment, the invention provides a compound having the formula:

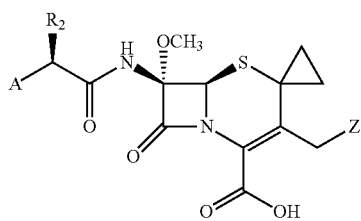

or an ester or a salt thereof.

In a further embodiment, the invention provides a compound having the formula:

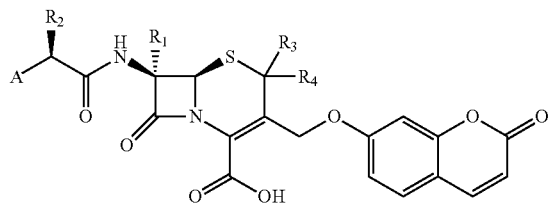

or an ester or a salt thereof.

In yet a further embodiment, the invention provides a compound having the formula:

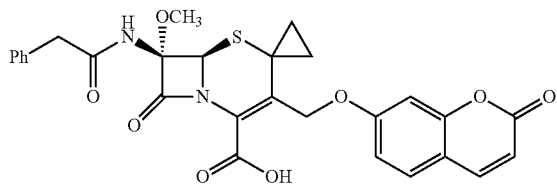 [SMILES: CO[C@@]1(NC(=O)Cc2ccccc2)C(=O)N2C(C(=O)O)=C(COc3ccc4ccc(=O)oc4c3)C3(CC3)S[C@@H]21]

or an ester or a salt thereof.

In certain embodiments, Z is a moiety that provides a fluorescent, luminescent, or colorimetric signal when released from the compound.

In certain embodiments, Z is a fluorescent moiety selected from a courmarin moiety, a xanthene moiety, a resorufin moiety, a cyanine moiety, a difluoroboradiazaindacene moiety, a bimane moiety, an acridine moiety, an isoindole moiety, a dansyl moiety, an aminophthalic hydrazide moiety, an aminophthalimide moiety, an aminonaphthalimide moiety, a quinine moiety, a dicyanovinyl moiety, a tricyanovinyl moiety, an indolaniline moiety, an indamine moiety, and derivatives thereof. In certain embodiments, Z is a xanthene moiety selected from a fluorescein moiety, a rhodol moiety, a rhodamine moiety, and derivatives thereof. In certain embodiments, Z is a luciferin moiety.

In another aspect, the invention provides methods for using the β-lactamase substrates of the invention.

In one embodiment, the invention provides a method for detecting β-lactamase in a sample. In the method, a sample is contacted with a compound of the invention, and an optical signal generated from contacting the sample with the compound is measured.

In another embodiment, the invention provides a method for diagnosing tuberculosis. In the method, a sample is contacted with a compound of the invention, and an optical signal generated from contacting the sample with the compound is measured.

In the methods, the sample may be sputum, pleural fluid, spinal fluid, blood, urine, saliva, stool, tissue biopsies, tissue homogenates, directly in live animals or human patients, or a sample obtained by swabbing an area of interest on a subject.

The method of the invention is useful for detecting pathogenic bacterial species such as *Bacteroides, Clostridium, Streptococcus, Staphylococcus, Pseudomonas, Haemophilus, Legionella, Mycobacterium, Escherichia, Salmonella, Shigella*, or *Listeria*.

In the methods, measuring the optical signal includes measuring fluorescence emission intensity, measuring absorbance intensity, measuring luminescence emission intensity, and observing a color change.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 2 is a comparison of β-lactamase kinetic parameters of fluorogenic probes. (Table 1).

FIGS. 4A and 4B compares time course of fluorescence intensity of CDG-3 and CDG-OMe in the presence of BlaC (1 fmol) (4A) and TEM-1 Bla (100 pmol) (4B). FIGS. 4C-4D illustrates enhanced fluorescence intensity of CDG-3 (10 μM) (4C) and CDG-OMe (10 μM) (4D) after 3 h incubation with a series of diluted β-lactamases. Inserts show a magnified view of the intensity at low pmol β-lactamase quantities. Data were collected in a 384-well plate with a total volume of 25 μL in each well. Fluorescence was measured with excitation at 490 nm and emission at 535 nm. Relative fluorescence represents the difference in fluorescence intensity with and without β-lactamase incubation. Data in FIGS. 4C-4D are the average of three replicate experiments. Error bars are ±SD.

FIG. 5A shows fluorescence intensity of CDG probes incubated with indicated β-lactamase-expressing bacteria for 3 h at room temperature. Fluorescence was measured with excitation at 490 nm and emission at 535 nm. FIG. 5B shows fluorescence imaging of indicated β-lactamase-expressing bacteria ($10^6$ c.f.u.) after incubation with CDG (10 μM) probes at room temperature for 3 h (excitation: 500 nm; emission 540 nm). From left to right: (1) Blank, (2) *E. coli*, (3) *K. pneumoniae* with SHV-18, (4) *E. cloacae* with AmpC, (5) *E. coli* transformed with BlaC, (6) *K. pneumoniae* with KPC, (7) *E. coli* with NDM-1, and (8) *E. coli* transformed with TEM-1 Bla. FIG. 5C illustrates detection of BCG with CDG-3 in human sputum obtained from cystic fibrosis patients (40 min).

DETAILED DESCRIPTION OF THE INVENTION

The present invention provides β-lactamase substrates and methods for using the substrates to detect β-lactamase and to diagnose tuberculosis. The substrates are useful as probes that can be used in optical methods to detect β-lactamase and to diagnose tuberculosis.

Figure 1A:
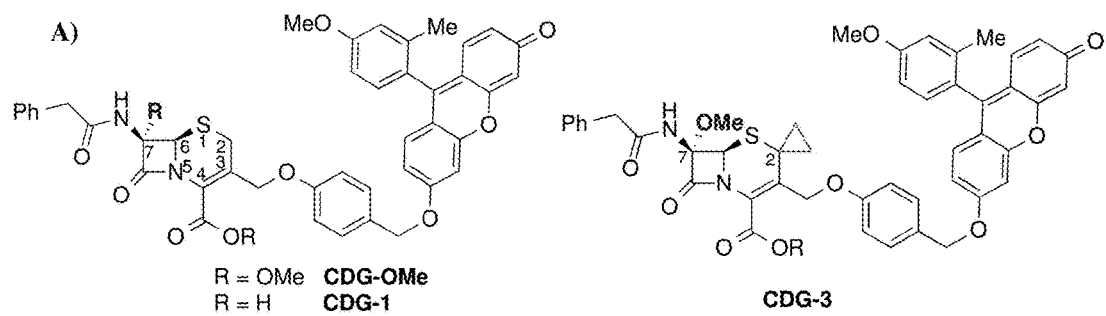
FIG. 1A illustrates the structural formulas of CDG-OMe, CDG-1, and CDG-3, a representative probe of the invention.

Recently, the crystal structure of BlaC has been solved and reveals a larger and more flexible active site than most β-lactamases. This important structural insight led to the hypothesis that BlaC can tolerate more bulky lactam substrates and these can serve as biomarkers for Mtb detection. Previously, a methoxy substitution was introduced to the 7-position of the lactam ring, and successfully developed a BlaC-specific fluorogenic substrate CDG-OMe (FIG. 1A). CDG-OMe has displayed preferred kinetics to BlaC over TEM-1 Bla by 8,900 fold in the catalytic efficiency of $k_{cat}/K_m$: $1.6 \times 10^5$ $s^{-1}M^{-1}$ for BlaC vs 18 $s^{-1}M^{-1}$ for TEM-1 Bla (Table 1, FIG. 2). The present invention provides an improved fluorogenic probe with greatly improved specificity to BlaC for the detection of Mtb. These new fluorogenic probes have catalytic efficiency by BlaC is 120,000 fold higher than TEM-1 Bla. In certain embodiments, the new probes have substitutions at the 2-position on the six-member ring of the cephalosporin core structure, in addition to previously identified BlaC-preferred 7-OMe substituent. These modifications in combination provide new probes with both faster BlaC kinetics and higher BlaC specificity than the previous probe CDG-OMe.

In the compounds of the invention, the cephalosporin backbone serves as a cleavable linker. In certain embodiments, the compounds of the invention include a single moiety (e.g., a chromophore, a luminophore, a fluorophore moiety) that generates an optical signal (e.g., absorbance, luminescence, fluorescence) when released from the compound.

In one aspect, the invention provides β-lactamase substrates.

In one embodiment, the invention provides a compound having Formula (I):

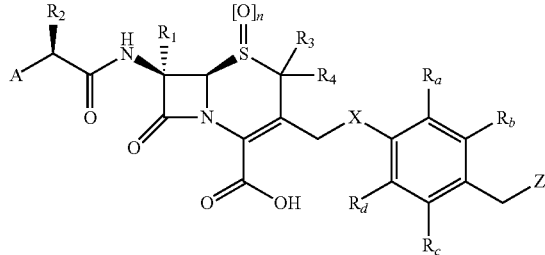

Formula (I)

or an ester or a salt thereof,
wherein
A is selected from the group consisting of:
(a) substituted and unsubstituted C6-C10 aryl, and
(b) substituted and unsubstituted C3-C7 heteroaryl;
$R_1$ is selected from the group consisting of:
(a) hydrogen,
(b) methoxy, and
(c) ethoxy;
$R_2$ is selected from the group consisting of hydrogen, C1-C3 alkyl, C1-C3 alkyl substituted with one or more halogens, and substituted piperazine;
$R_3$ and $R_4$ are independently selected from the group consisting of hydrogen, methyl, ethyl, propyl, halomethyl (e.g., —$CH_2$—X), haloethyl (e.g., —$CH_2CH_2$—X or —CHX—$CH_3$), halopropyl (e.g., —$CH_2CH_2CH_2$—X, —$CH_2$CHX—$CH_3$, or —CHX$CH_2$—$CH_3$), or $R_3$ and $R_4$ taken together with the carbon atom to which they are attached form a cyclopropyl or a cyclobutyl ring, provided that $R_3$ and $R_4$ are not both hydrogen;

n is 0 or 1;

$R_a$, $R_b$, $R_c$, and $R_d$ are independently selected from the group consisting of hydrogen, halogen (e.g., F, Cl, Br, I), nitro, cyano, C1-C3 alkyl (e.g., methyl), and C1-C3 alkyl substituted with one or more halogens (e.g., trifluoromethyl); and Z is a reporting group that provides an optical signal when released from the compound.

In certain embodiments, n is 0.

In one embodiment, the invention provides a compound having the Formula (II):

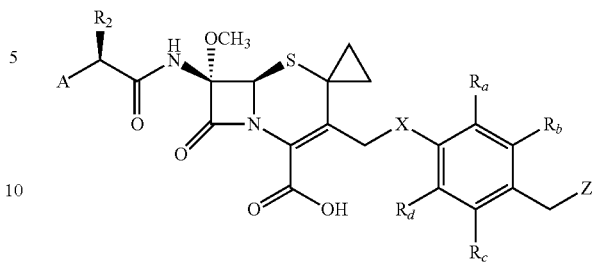

Formula (II)

or an ester or a salt thereof, wherein $R_2$, $R_a$-$R_d$, and Z are as defined above for Formula (I).

In another embodiment, the invention provides a compound having the Formula (III):

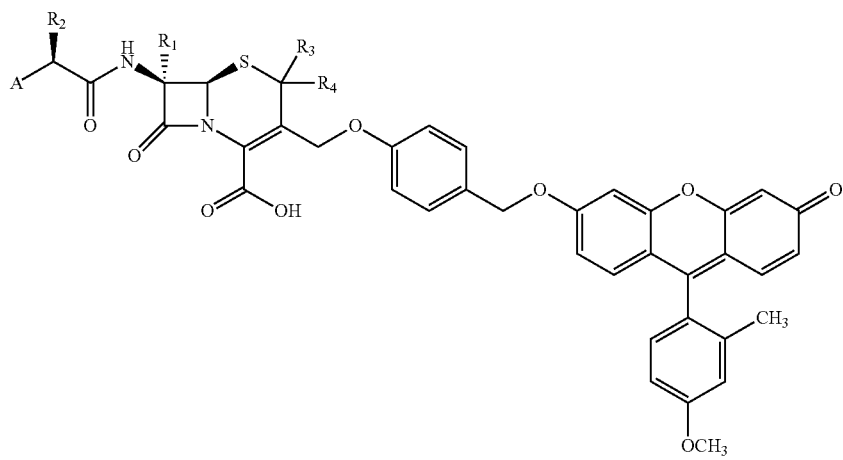

Formula (III)

or an ester or a salt thereof, wherein $R_1$-$R_4$ are as defined above for Formula (I).

In a further embodiment, the invention provides a compound having the Formula (IV):

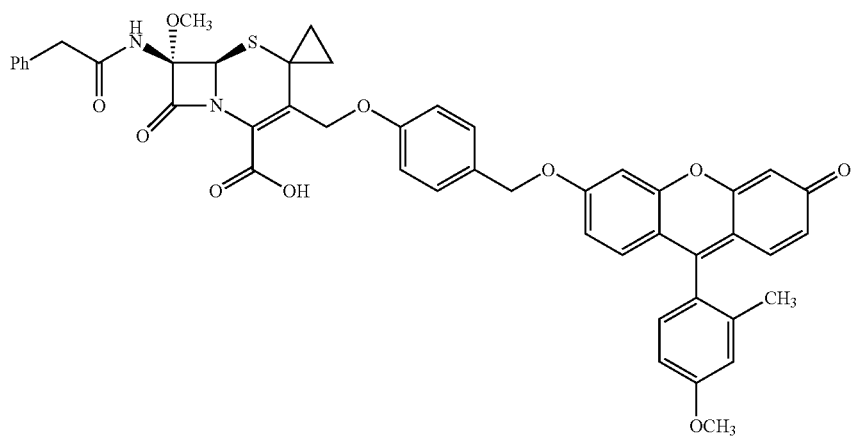

Formula (IV)

or an ester or a salt thereof.

In one embodiment, the invention provides a compound having Formula (V):

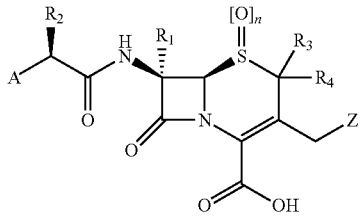

Formula (V)

or an ester or a salt thereof, wherein

A is selected from the group consisting of:

(a) substituted and unsubstituted C6-C10 aryl, and (b) substituted and unsubstituted C3-C7 heteroaryl;

$R_1$ is selected from the group consisting of:

(a) hydrogen, (b) methoxy, and (c) ethoxy;

$R_2$ is selected from the group consisting of hydrogen, C1-C3 alkyl, C1-C3 alkyl substituted with one or more halogens, and substituted piperazine;

$R_3$ and $R_4$ are independently selected from the group consisting of hydrogen, methyl, ethyl, propyl, halomethyl (e.g., —CH$_2$—X), haloethyl (e.g., —CH$_2$CH$_2$—X or —CHX—CH$_3$), halopropyl (e.g., —CH$_2$CH$_2$CH$_2$—X, —CH$_2$CHX—CH$_3$, or —CHXCH$_2$—CH$_3$), or $R_3$ and $R_4$ taken together with the carbon atom to which they are attached form a cyclopropyl or a cyclobutyl ring, provided that $R_3$ and $R_4$ are not both hydrogen;

n is 0 or 1; and

Z is a reporting group that provides an optical signal when released from the compound.

In certain embodiments, n is 0.

In one embodiment, the invention provides a compound having Formula (VI):

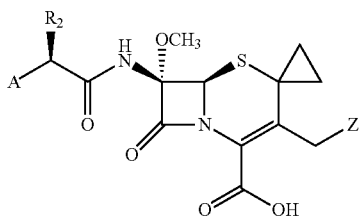

Formula (VI)

or an ester or a salt thereof, wherein $R_2$ and Z are as defined above for Formula (V).

In another embodiment, the invention provides a compound having Formula (VII):

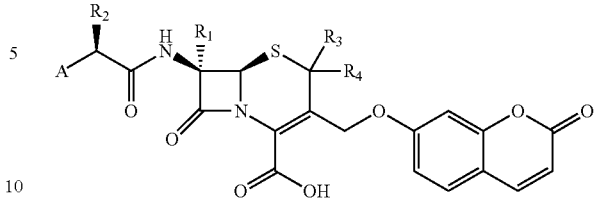

Formula (VII)

or an ester or a salt thereof, wherein $R_1$-$R_4$ are as defined above for Formula (V).

In a further embodiment, the invention provides a compound having Formula (VIII):

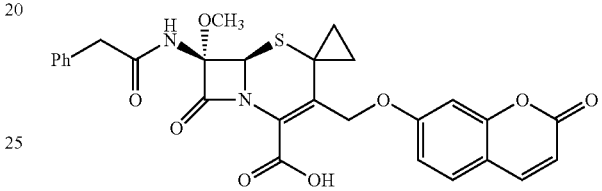

Formula (VIII)

or an ester or a salt thereof.

In certain embodiments, for the compounds of Formulae (I), (II), (III), (V), (VI), and (VII), A is phenyl.

In certain embodiments, for the compounds of Formulae (I), (II), (III), (V), (VI), and (VII), $R_2$ is hydrogen.

In certain embodiments, for the compounds of Formulae (I), (III), (V), and (VII), $R_1$ is methoxy.

In certain embodiments, for the compounds of Formulae (I), (III), (V), and (VII), $R_3$ and $R_4$ taken together with the carbon atom to which they are attached form a cyclopropyl ring.

In certain embodiments, for the compounds of Formula (I), $R_a$, $R_b$, $R_c$, and $R_d$ are independently selected from the group consisting of hydrogen, fluoro, cyano, and methyl. In certain of these embodiments, the compounds of Formula (I) are 2-methyl-1,4-phenylene, 3-methyl-1,4-phenylene, 2-fluoro-1,4-phenylene, 3-fluoro-1,4-phenylene, and 2-cyano-1,4-phenylene compounds.

The compounds of Formulae (I)-(VIII) include a carboxylic acid group. It will be appreciated that salts and esters of the compounds are also within the scope of the invention. Suitable salts include metal ions (e.g., sodium, potassium, lithium, magnesium, calcium) as well as nitrogen-based cations (e.g., ammonium). Suitable esters include alkyl (e.g., C1-C10), aryl (e.g., C6-C20), and aralkyl (e.g., C6-C20) esters.

In Formulae (I)-(III) and (V)-(VII), A is substituted and unsubstituted C6-C10 aryl or substituted and unsubstituted C3-C7 heteroaryl. Aryl and heteroaryl groups are defined below. These groups may be substituted with halogen, nitro, C1-C3 alkyl, C1-C3 alkyl substituted with one or more halogens, C1-C3 alkoxy, and C1-C3 alkoxy substituted with one or more halogens.

For the compounds of Formulae (I)-(III) and (V)-(VII), in certain embodiments, A is phenyl. In certain embodiments, $R_1$ is methoxy. In certain embodiments, substituted piperazine is

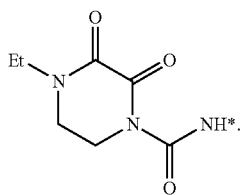

In the compounds of Formulae (I), (II), (V), and (VI), Z is a moiety that provides a fluorescent, luminescent, or colorimetric signal when released from the compound. As used herein the phrase "when released from the compound" refers to a product of enzymatic action (β-lactamase) on the compounds of the invention. Enzymatic action cleaves the cephalosporin backbone and releases a product that provides an optical signal thereby signaling cleavage and the presence of the enzyme.

In certain embodiments, Z is a fluorescent moiety. Representative fluorescent moieties useful in the compounds of the invention include those known in the art such as those described in U.S. Pat. Nos. 7,427,680, 7,396,926, 5,955,604, US 2007/0020715, US 2005/0181469, each expressly incorporated herein by reference in its entirety. Representative fluorescent phenolic dyes useful for making the compounds of the invention include those known in the art such as those describes in U.S. Pat. No. 7,427,680 (see, for example, FIG. 7).

In certain embodiments, a chemiluminescence readout can also be generated by use of the adamantylidene-dioxetane. The release of the free phenol from the substrate triggers spontaneous fragmentation of the dioxetane and emission of light. Alternatively, colored or fluorescent precipitates result from the indolyl or 2-(2-hydroxyphenyl) quinazolin-4-one substrates. Release of the free phenol triggers oxidation of 3-hydroxyindoles to blue indigo precipitates. The free 2-(2-hydroxyphenyl) quinazolin-4-one likewise forms a brightly fluorescent precipitate.

As noted above, a variety of fluorescent phenolic dye moieties are useful in making the compounds of the invention (e.g., courmarins, pyrenes, rhodols, and resorufins). In each case the fluorescence is greatly enhanced and shifts to longer wavelengths when the free phenolic group is release from the substrate. Suitable fluorescent moieties include fluorescent phenolic dye moieties such as xanthene moieties. Representative xanthene moieties include fluorescein moieties, rhodol moieties, and rhodamine moieties.

Representative Z groups include courmarin, xanthene, resorufin, cyanine, difluoroboradiazaindacene, bimane, acridine, isoindole, dansyl, aminophthalic hydrazide, aminophthalimide, aminonaphthalimide, quinine, dicyanovinyl, tricyanovinyl, indolaniline, and indamine moieties, and derivatives thereof. As used herein the term "derivatives thereof" refers to substitutions on the named moiety, typically on the ring structure with halogen and lower alkyl groups, that do not significantly alter the moiety's optical properties and that do not significantly alter the compound's substrate properties.

In one embodiment, Z is

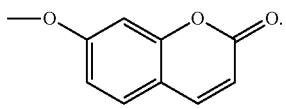

In another embodiment, Z is

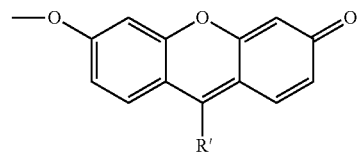

wherein R' is hydrogen or aryl (e.g., phenyl or substituted phenyl). Phenyl substituents include halogen, nitro, C1-C3 alkyl, C1-C3 alkyl substituted with one or more halogens, C1-C3 alkoxy, and C1-C3 alkoxy substituted with one or more halogens.

In a further embodiment, Z is

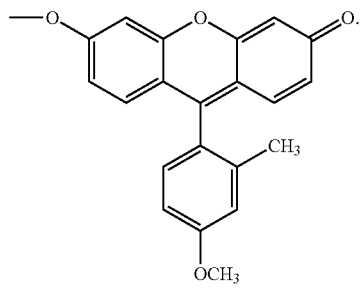 [SMILES: COc1ccc(-c2c3ccc(=O)cc-3oc3cc(OC)ccc23)c(C)c1]

The following are definitions of terms used herein.

The term "alkyl" refers to straight, branched, and cyclic aliphatic groups of 1 to 8 carbon atoms such as from 1 to 6 carbon atoms and 1 to 3 carbon atoms.

The term "aryl" refers to an aromatic group having from six to ten carbon atoms in the aromatic ring. Representative aryl groups include phenyl and naphthyl groups.

The term "heteroaryl" refers to aryl groups that include one or more ring heteroatoms (O, N, S). Representative heteroaryl groups include CSN, C4N, C4O, C4S, C3N2, C3NO, C3N groups (e.g., pyridyl, pyrrolyl, furan, thiophenyl, and imidazolyl groups).

The terms "halomethyl," "haloethyl," and "halopropyl" refer to methyl, ethyl, and propyl groups in which one or more hydrogens have been replaced with a halogen, such as fluorine, chlorine, bromine, of iodine. In certain embodiments, the "halo" of the halomethyl, haloethyl, and halopropyl groups is fluoro. In other embodiments, the "halo" group is chloro. Representative groups include monohalo groups, such as —CH$_2$—X, —CH$_2$CH$_2$—X, —CHX—CH$_3$, —CH$_2$CH$_2$CH$_2$—X, —CH$_2$CHX—CH$_3$, and —CHXCH$_2$—CH$_3$), where X is halo (e.g., fluoro). Halomethyl, haloethyl, and halopropyl groups also include perhalo groups such as perfluorogroups (e.g., —CF$_3$, —CF$_2$CF$_3$, and —CF$_2$CF$_2$CF$_3$.

The term "dye" refers to a molecule or part of a compound that absorbs specific frequencies of light, including but not limited to ultraviolet, visible, and near-infrared light. Dyes include phenolic dyes, such as, for example, umbelliferone, fluorescein, and resorufin; aromatic amines, and other compounds, such as, for example, rhodamine. The terms "dye" and "chromophore" are synonymous.

The terms "fluorophore," "fluorescent moiety" refers to a chromophore (light absorbing compound or moiety that fluoresces (emits light upon excitation).

Methods of Using the β-Lactamase Substrates

In another aspect of the invention, methods for detecting β-lactamase are provided. In one embodiment, the method includes contacting a sample to be analyzed with substrate of the invention, and measuring an optical signal generated from contacting the sample with the compound (e.g., measuring absorbance, luminescence, chemiluminescence, fluorescence emission intensity). In the method, the measured optical signal is indicative of the presence of β-lactamase in the sample.

In a further aspect of the invention, methods for diagnosing tuberculosis are provided. In one embodiment, the method includes contacting a sample to be analyzed with substrate of the invention, and measuring an optical signal generated from contacting the sample with the compound (e.g., measuring absorbance, luminescence, bioluminescence, chemiluminescence, fluorescence emission intensity). In the method, the measured optical signal (e.g., fluorescence emission intensity) is indicative of the presence of tuberculosis in the sample.

In the methods noted above, suitable samples include sputum, pleural fluid, spinal fluid, blood, urine, saliva, stool, tissue biopsies, tissue homogenates, directly in live animals or human patients, or a sample obtained by swabbing an area of interest on a subject.

Suitable samples for analysis by the methods of the invention can include a pathogenic bacterial species that express β-lactamase or another enzyme that a similar fluorogenic probe can be produced for such as *Bacteroides, Clostridium, Streptococcus, Staphylococcus, Pseudomonas, Haemophilus, Legionella, Mycobacterium, Escherichia, Salmonella, Shigella*, or *Listeria*.

In certain embodiments, measuring fluorescence emission intensity comprises exciting the sample with light having a wavelength in the range from about 300 nm to about 900 nm. In other embodiments, wherein measuring fluorescence emission intensity comprises exciting the sample with light having a wavelength in the range from about 540 nm to about 730 nm.

In certain embodiments, measuring fluorescence emission intensity comprises measuring emission at a wavelength in the range from about 300 nm to about 900 nm. In other embodiments, measuring fluorescence emission intensity comprises measuring emission at a wavelength in the range from about 650 nm to about 800 nm.

In further aspects, the present invention provides methods for detecting a pathogenic bacteria in real time in a subject using β-lactamase substrates of the invention. The methods include introducing into the subject or a biological sample therefrom a fluorescent, luminescent or colorimetric substrate of the pathogenic bacteria and imaging the subject or sample for a product from β-lactamase activity on the substrate. Signals at a wavelength emitted by the β-lactamase product are acquired thereby detecting the pathogenic bacteria in the subject. The present invention provides a related method that includes producing a 3D reconstruction of the emitted signal to determine location of the pathogenic bacteria in the subject. The present invention also provides a method further comprising diagnosing in real time a pathophysiological condition associated with the pathogenic bacteria based on an emitted signal intensity greater than a measured control signal.

In one embodiment of the present invention there is provided a method for detecting a pathogenic bacteria in real time in a subject, comprising introducing into the subject or a biological sample therefrom a fluorescent, luminescent or colorimetric substrate of the pathogenic bacteria; imaging the subject or sample at an excitation wavelength for a product from β-lactamase activity on the substrate; and acquiring signals at a wavelength emitted by the β-lactamase product; thereby detecting the pathogenic bacteria in the subject.

Further to this embodiment, the method comprises producing a 3D reconstruction of the emitted signal to determine location of the pathogenic bacteria in the subject. In another further embodiment the method comprises diagnosing in real time a pathophysiological condition associated with the pathogenic bacteria based on an emitted signal intensity greater than a measured control signal. An example of a pathophysiological condition is tuberculosis.

In all embodiments the imaging or excitation wavelengths and the emission wavelength independently may be from about 300 nm to about 900 nm. In certain embodiments, the imaging or excitation wavelength is from about 540 nm to about 730 nm and the emitted signals may be about 650 nm to about 800 nm. In certain embodiments, colorimetric indication may be visually identified by the human eye by a color change or measured by equipment to determine an assigned numerical value.

In a related embodiment, the invention provides a method for imaging a pathogenic bacteria that includes introducing into a subject or contacting a biological sample therefrom or obtained from a surface with a substrate for a β-lactamase of the pathogenic bacteria; delivering to the pathogenic bacteria an excitation wavelength for a product of β-lactamase activity on the substrate; acquiring fluorescent, luminescent, or colorimetric signals emitted from the product; and producing a 3D reconstruction of the acquired signals, thereby imaging the pathogenic bacteria. In aspects of this embodiment, the pathogenic bacteria may be contacted in vivo or in vitro with the substrates.

In another related embodiment, the invention provides a method for detecting a pathogenic bacteria in real time that includes introducing into the subject or a biological sample therefrom a substrate for a β-lactamase of the pathogenic bacteria; imaging the subject or sample for a product from β-lactamase activity on the substrate; and acquiring signals at a wavelength emitted by the beta-lactamase product; thereby detecting the pathogenic bacteria in the subject. Further to this embodiment, the method comprises producing a 3D reconstruction of the emitted signal to determine location of the pathogenic bacteria in the subject. In another further embodiment, the method may include quantifying and differentiating infected cells from non-infected cells in the biological sample. The steps of differentiating and/or quantifying infected cells is performed by utilizing one or more of flow cytometry, confocal microscopy, or fluorescent spectrometry.

In another embodiment, the invention provides a method for diagnosing a pathophysiological condition associated with pathogenic bacteria in a subject that includes administering to the subject a fluorogenic or luminescent substrate for a β-lactamase of the pathogenic bacteria; imaging the subject at an excitation wavelength for a product of β-lactamase activity on the substrate; and measuring in real time a fluorescent, luminescent, or colorimetric signal intensity at wavelength emitted by the product; wherein a fluorescent, luminescent or colorimetric signal intensity greater than a measured control signal correlates to a diagnosis of the pathophysiological condition. Further to this embodiment, the method includes producing a 3D reconstruction of the signal to determine the location of the microbial pathogen. In another further embodiment, the method includes administering one or more therapeutic compounds effective to treat the pathophysiological condition. Further still, the method includes re-administering the fluorogenic or luminescent substrate to the subject; and re-imaging the subject to monitor the efficacy of the therapeutic compound; wherein a decrease in emitted signal compared to the signal at diagnosis indicates a therapeutic effect on the pathophysiological condition.

In a related embodiment, the invention provides a method for diagnosing a pathophysiological condition associated with a pathogenic bacteria in a subject that includes administering to the subject or contacting a biological sample derived therefrom with a substrate for a β-lactamase of the pathogenic bacteria; imaging the subject for a product of β-lactamase activity on the substrate; and measuring in real time a signal intensity at a wavelength emitted by the product; wherein a signal intensity greater than a measured control signal correlates to a diagnosis of the pathophysiological condition. Further to this embodiment, the method comprises producing a 3D image and administering therapeutic compound(s) appropriate for the diagnosed pathophysiological condition and re-administering the substrate. In another further embodiment the method includes one or both of quantifying and differentiating infected cells from non-infected cells in the biological sample.

In another related embodiment of the present invention there is provided a method of diagnosing a pathophysiological condition associated with a pathogenic bacteria in a subject, that includes contacting a sample obtained from said subject with a colorimetric substrate for a β-lactamase of the pathogenic bacteria; wherein a product of β-lactamase activity on the substrate causes a change of color visible to the naked eye, thus indicating diagnosis.

In yet another embodiment, the invention provides a diagnostic method for detecting a mycobacterial infection in a subject, comprising obtaining a biological sample from the subject; contacting the biological sample with a fluorogenic substrate of a mycobacterial β-lactamase enzyme; imaging the biological sample for a product of β-lactamase activity on the fluorogenic substrate; and measuring a signal intensity at a wavelength emitted by the product; wherein a signal intensity greater than a measured control signal indicates the presence of the mycobacterial infection. Further to this embodiment, the method provides repeating the above method steps one or more times to monitor therapeutic efficacy of a treatment regimen administered to the subject upon detection of the mycobacterial infection; wherein a decrease in the measured fluorescent signal compared to control correlates to a positive response to the treatment regimen. In another further embodiment, the method includes one or both of quantifying and differentiating infected cells from non-infected cells in the biological sample.

In yet another embodiment, the invention provides a method for screening for therapeutic compounds effective for treating a pathophysiological condition associated with a pathogenic bacteria in a subject that includes selecting a potential therapeutic compound for the pathogenic bacteria; contacting the bacterial cells with a fluorescent, luminescent, or colorimetric substrate; contacting the bacterial cells with the potential therapeutic compound; and measuring a fluorescent, luminescent, or colorimetric signal produced by the bacterial cells in the presence and absence of the potential therapeutic compound; wherein a decrease in signal in the presence of the therapeutic compound compared to the signal in the absence thereof indicates a therapeutic effect of the compound against the pathogenic bacteria.

In a related embodiment, the invention provides a method for screening for therapeutic compounds effective for treating a pathophysiological condition associated with a pathogenic bacteria in a subject that includes selecting a potential therapeutic compound for the pathogenic bacteria; contacting the bacterial cells or a biological sample comprising the same with a substrate of a bacterial β-lactamase thereof; contacting the bacterial cells or the biological sample comprising the same with the potential therapeutic compound; and measuring a fluorescent, luminescent, or colorimetric signal produced by the bacterial cells in the presence and absence of the potential therapeutic compound; wherein a decrease in signal in the presence of the therapeutic compound compared to the signal in the absence thereof indicates a therapeutic effect of the compound against the pathogenic bacteria.

In yet another embodiment, the invention provides an assay device for visibly detecting a pathogenic bacteria in a biological sample that includes a platform having means for receiving an incubation mixture comprising the biological sample and a color-producing substrate for a β-lactamase enzyme associated with the pathogenic bacteria and means for capturing and concentrating a colored product produced by the β-lactamase activity upon the substrate in fluid connection to the receiving means. Further to this embodiment the assay device may comprise a means for allowing only the colored product to flow downstream from the receiving means. In another further embodiment the assay device may include an internal control downstream from the receiving means. In yet another further embodiment, the assay device may comprise means for absorbing fluid downstream from the receiving means.

In yet another embodiment, the invention provides an assay method for determining drug susceptibility of pathogenic bacteria in a subject infected by said pathogenic bacteria that includes obtaining a biological sample from the subject; contacting said biological sample with a drug effective against the pathogenic bacteria; contacting said biological sample with a substrate for a β-lactamase of the pathogenic bacteria; delivering an excitation wavelength to the biological sample; and measuring levels of a signal intensity at an emission wavelength produced by the product of the β-lactamase action on the substrate in the biological sample over a period of time; wherein no increase or a decrease in signal intensity levels over the time period correlates to susceptibility of the pathogenic bacteria to the drug. Further to this embodiment, the method includes plating aliquots from the biological sample over the period of time to monitor colony formation of the pathogenic bacteria. In another further embodiment, the method includes one or both of quantifying and differentiating infected cells from non-infected cells in the biological sample. In yet another further embodiment, the method includes monitoring for acquisition of resistance to the drug by the pathogenic bacteria by the steps of obtaining a biological sample after a treatment period with the drug; and repeating the process steps; wherein an increase in signal intensity levels over the time period correlates to resistance to the drug. In all embodiments the measuring step may comprise acquiring the signals at intervals during a time period of about 24 hours and reading and recording the intensity thereof.

In yet another embodiment, the invention provides an in vitro method for determining drug susceptibility of a pathogenic Mycobacteria in a subject infected by the same that includes the steps of obtaining a biological sample from the subject; contacting said biological sample with an anti-mycobacterial drug; contacting said biological sample with a fluorogenic substrate for Mycobacterial β-lactamase; delivering an excitation wavelength to the biological sample; and measuring levels of fluorescence at an emission wavelength produced by a fluorescent product of the β-lactamase action on the substrate in the biological sample over a period of time; wherein no increase or a decrease in fluorescence over the time period correlates to susceptibility of the pathogenic bacteria to the drug. Further to this embodiment, the method comprises the plating step and the quantifying and/or differentiating steps. In another further embodiment, the method comprises monitoring for acquisition of resistance to the anti-Mycobacterial drug by the Mycobacteria by the steps of obtaining a biological sample after a treatment period with the Mycobacterial drug; and repeating the process steps; wherein an increase in fluorescence levels over the time period correlates to resistance to the Mycobacterial drug. In all embodiments, the measuring step may comprise acquiring the signals at intervals during a time period of about 24 hours and reading and recording the intensity thereof.

In yet another embodiment, the invention provides an assay system for monitoring drug susceptibility of pathogenic bacteria that includes one or more color-producing substrates for a β-lactamase of the pathogenic bacteria; an assay device for visibly detecting a product of β-lactamase activity on the substrate; and a reader configured to quantify visible signals emitted by the detected product. In this embodiment, the assay device comprises a platform having means for receiving an incubation mixture comprising a biological sample of the pathogenic bacteria, a drug effective against the pathogenic bacteria, and the fluorescent, luminescent, or color-producing substrate and means for capturing and concentrating a colored product produced by the β-lactamase activity upon the substrate in fluid connection to the receiving means. Further to this embodiment the assay device may means for allowing only the colored product to flow downstream from the receiving means. Further still to this embodiment, the assay device may include an internal control downstream from the receiving means. Further still to this embodiment, the assay device may include means for absorbing fluid downstream from the receiving means.

The in vivo imaging systems useful for carrying out the methods of the invention may detect a fluorescent, a luminescent, or a colorimetric signal produced by the substrate for β-lactamase activity. Suitable imaging systems are known in the art and commercially available; for example, a sequential reporter-enzyme fluorescence (SREF) system, a sequential reporter-enzyme luminescence (SREL) system, or a bioluminescent system may be used to detect products of β-lactamase activity. Furthermore, the acquired signals may be used to produce a 3D representation useful to locate the bacterial pathogen. For these systems, one of ordinary skill in the imaging arts is well able to select excitation and emission wavelengths based on the compound and/or reporter used and the type of signal to be detected. Generally, both the excitation or imaging wavelength and the emission wavelength may be about 300 nm to about 900 nm. An example of an excitation signal may be within a range of about 540 nm to about 730 nm and an emission signal within about 650 nm to about 800 nm. It also is contemplated that in vivo imaging systems of the present invention may also detect other signals, such as produced by radiation, or any detectable or readable signal produced by β-lactamase activity upon a suitable substrate or other detection agents.

The systems and methods described herein are effective to detect, locate, quantify, and determine viability of a bacterial pathogen in real time. Imaging may be performed in vitro with a cell culture or single cultured cell or ex vivo with a clinical sample or specimen using the SREL or SREF or in vivo within a subject using any of the disclosed imaging systems. Samples used in vitro may include, but are not restricted to biopsies, pleural fluid, sputum and other body fluids inclusive of blood, saliva, urine and stool that may have the bacterial pathogen. Thus, the systems and methods provided herein are effective to diagnose a pathophysiological condition, such as a disease or infection, associated with a bacterial pathogen. Because very low levels, including a single bacterium, can be detected, diagnosis can be immediate and at an earlier point of infection than current diagnostic methods. The systems and methods described herein may be utilized for testing and regular screening of health care workers who may be at risk of bacterial infection. Additionally, these systems and methods can also be used for screening and detecting contamination on instruments, utensils, facilities, work surfaces, clothing, and people. Because methicillin-resistant *Staphylococcus aureus* (MRSA) infections are present on up to 40% of health care workers and major areas of infection are nasal passages and cracks in hands caused by over washing, the invention is useful as a screening method for bacterial pathogens in healthcare centers and workers. These systems and methods may be used in agricultural and zoological applications for detection of β-lactamase.

Also, correlation of signal strength to quantity of bacteria is well within the limits of current imaging technology. Thus, efficacy of compounds, drugs, pharmaceutical compositions, or other therapeutic agents can be monitored in real time. The systems and methods described herein thus provide a high-throughput system for screening antibacterial agents. Because the detection of β-lactamase requires bacterial viability, enzyme levels in the presence of one or more therapeutic agents provide a measure of antimicrobial activity. Use of substrates appropriate for the particular bacteria allows rapid measurement of changes in β-lactamase levels and nearly immediate determination of the effectiveness of the therapeutic agent. Throughput systems are useful for single samples to thousands at a time in microplates.

More particularly, the REF systems are useful for many other in vitro methods for detecting and quantifying infected cells, using flow cytometer, confocal microscopy, and or fluorescent spectrometer. Once the β-lactamase substrate is in cells, β-lactamase secreted by the intracellular bacteria cleaves the beta-lactam ring thus labeling the infected cells with a detectable agent. Using flow-cytometry, the infected and non-infected cells can be differentiated and quantified.

Furthermore, the invention provides assays, in vitro methods, and systems for determining or monitoring drug susceptibility in the pathogenic bacteria described herein or detecting an acquisition of drug resistance in the same. The β-lactamase substrates described herein are well-suited for assays for drug susceptibility.

Representative methods, assays, and systems useful for carrying out the methods, assays, and systems of the invention using the β-lactamase substrates described herein are described in application Ser. No. 14/044,825, filed Oct. 2, 2013, expressly incorporated herein by reference in its entirety.

The following is a description of the preparation and use of representative β-lactamase substrates of the invention.

Figure 1B:
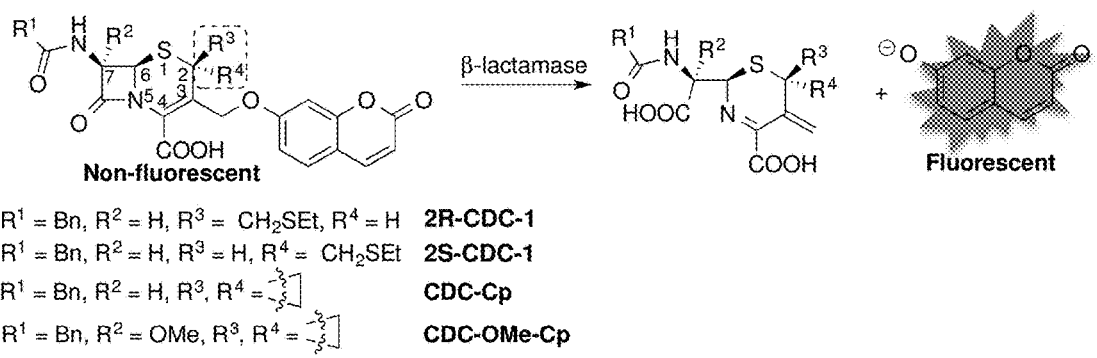
FIG. 1B is a schematic illustration of fluorescence detection of β-lactamase activity by CDC series probes.
Figure 11:
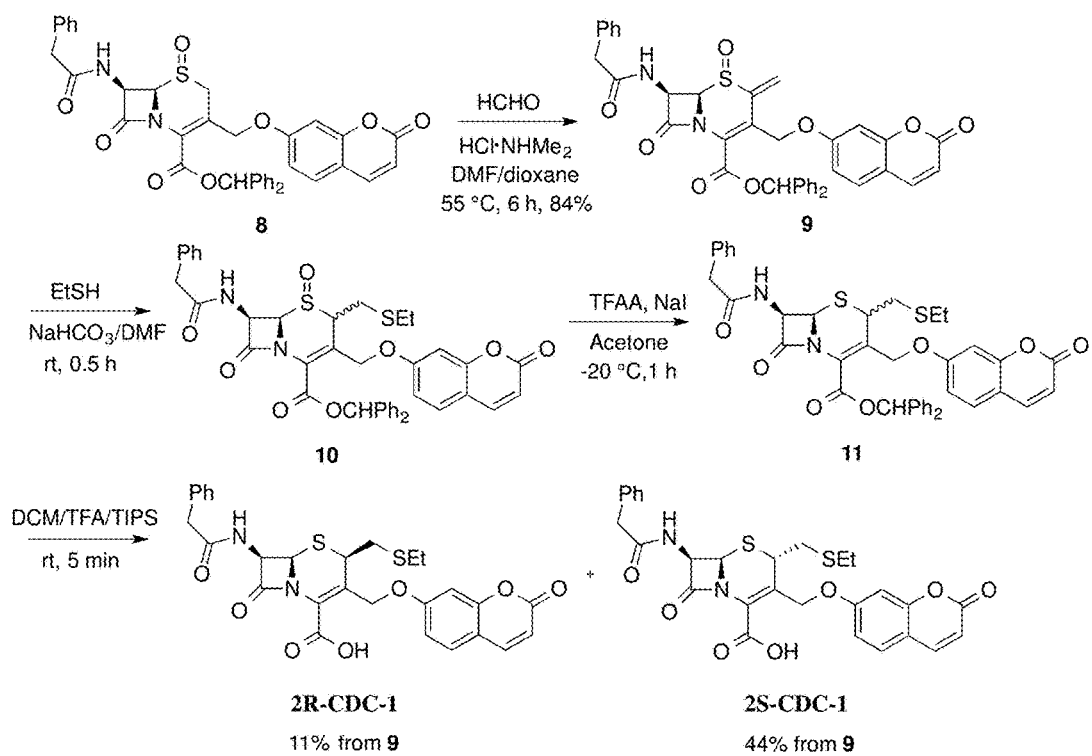
FIG. 11 is a schematic illustration of the synthesis of 2R-CDC-1 and 2S-CDC-1.

To probe the effect of a substitution off the β-lactam unit at the 2-position on the substrate hydrolysis kinetics by β-lactamases, a coumarin-based non-specific β-lactamase fluorogenic substrate (CDC-1) was modified to include a 2-ethylthiomethyl substitution that produced two epimers ((2R-CDC-1, 2S-CDC-1)) (FIG. 1B, FIG. 11).

Both CDC-1 analogues can be hydrolyzed by BlaC and TEM-1 Bla, concurrently releasing the free coumarin dye and thus generating blue fluorescent signal. The catalytic constant ($k_{cat}$) and the Michaelis constant ($K_m$) of BlaC and TEM-1 Bla were then determined as shown in Table 1 (FIG. 2). Advantageously, BlaC appeared to tolerate the 2-substituent well in comparison to CDC-1 ($1.1 \times 10^5$ s$^{-1}$M$^{-1}$ for 2R-CDC-1 and $1.2 \times 10^5$ s$^{-1}$ M$^{-1}$ for 2S-CDC-1, vs $2.1 \times 10^5$ s$^{-1}$M$^{-1}$ for CDC-1, Table 1, FIG. 2), and the stereo conformation of the ethylthiomethyl produced little difference in the BlaC catalytic efficiency. However, the hydrolysis kinetics of 2S-CDC-1 by TEM-1 Bla ($4 \times 10^4$ s$^{-1}$M$^{-1}$, Table 1, FIG. 2) was 10-fold less efficient than CDC-1 ($3.6 \times 10^5$ s$^{-1}$M$^{-1}$), while the other isomer 2R-CDC-1 showed similar TEM-1 Bla kinetics ($2.7 \times 10^5$ s$^{-1}$M$^{-1}$) to CDC-1. This result indicated that the 2-substitution with the S conformation enhanced the substrate selectivity for BlaC and that the R conformation did not significantly impact the hydrolysis kinetics much.

The effect on the hydrolysis kinetics if both protons at the 2-position are replaced with dual substitutions was examined. Besides the potential selectivity for BlaC, there is an important advantage with the replacement of both protons because it will avoid the well precedented, undesired isomerization from the 3,4-double bound to the 2,3-position, which would otherwise lead to the loss of probe activity. A cylcopropyl group was introduced to afford CDC-Cp (see FIG. 12). Kinetic measurements revealed that CDC-Cp showed around 10-fold higher specificity for BlaC than TEM-1 Bla ($k_{cat}/K_m$: $1.9 \times 10^5$ s$^{-1}$M$^{-1}$ for BlaC vs $2.2 \times 10^4$ s$^{-1}$M$^{-1}$ for TEM-1 Bla, Table 1, FIG. 2).

To enhance selectivity, 2-substitution was combined with 7-substitution. CDC-OMe-Cp was synthesized for evaluation and displayed remarkable BlaC specificity: its catalytic efficiency for BlaC ($4.4 \times 10^4$ s$^{-1}$M$^{-1}$) is $6.3 \times 10^4$ times higher than for TEM-1 Bla (0.7 s$^{-1}$M$^{-1}$).

Figure 3:
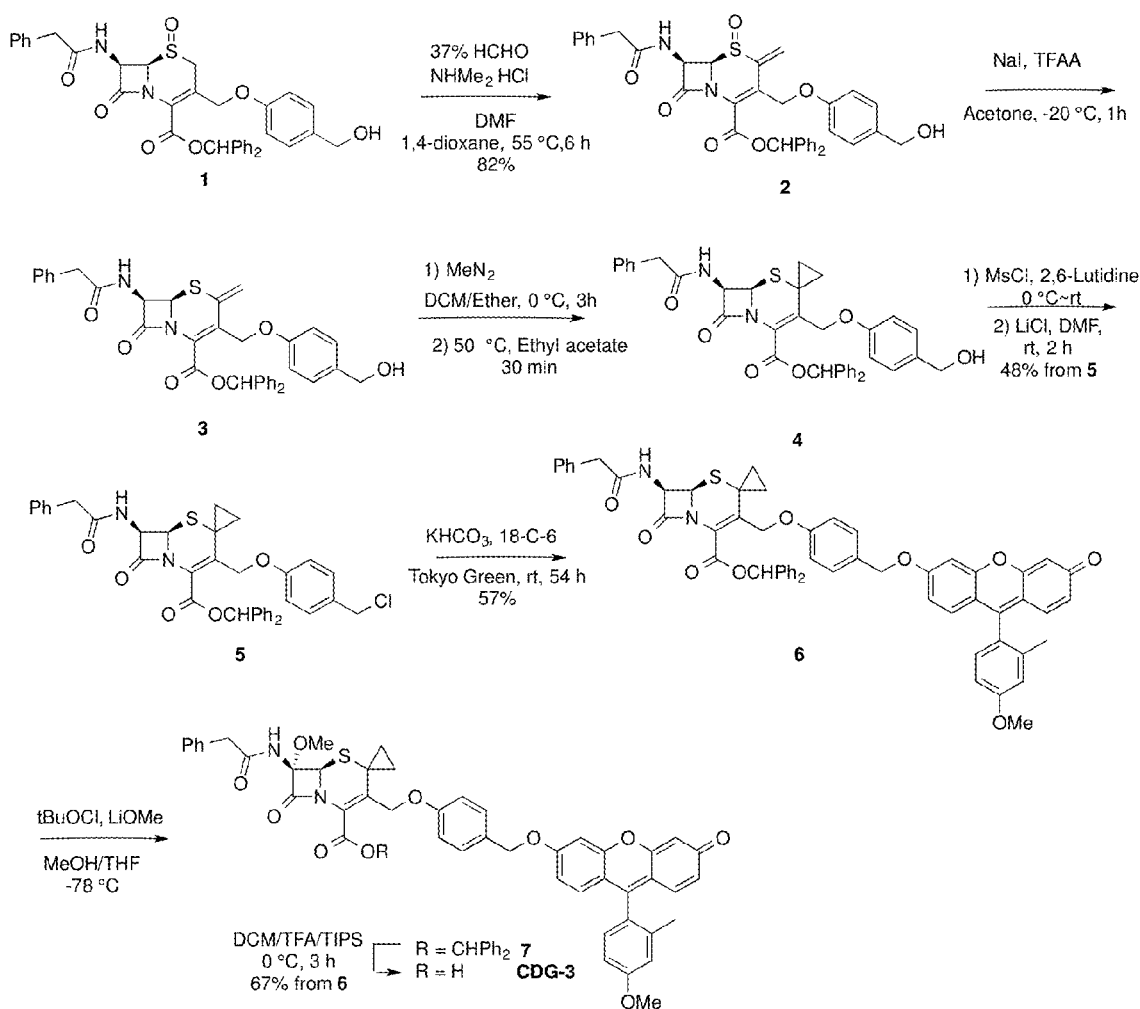
FIG. 3 is a schematic illustration of the synthesis of CDG-3, a representative probe of the invention.
Figure 4A:
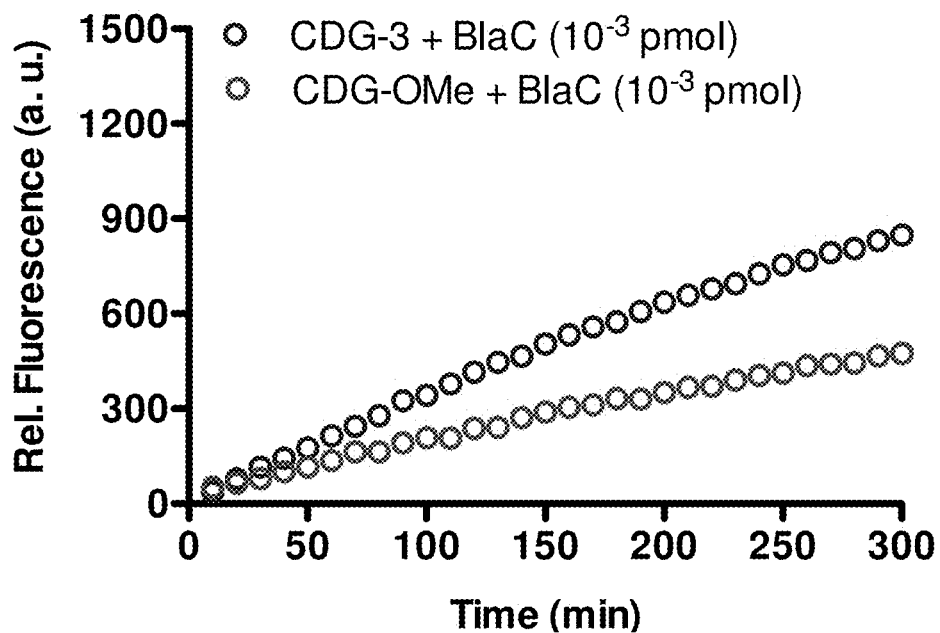
FIGS. 4A-4D compare β-lactamase selectivity of CDG-3 and CDG-OMe.
Figure 4B:
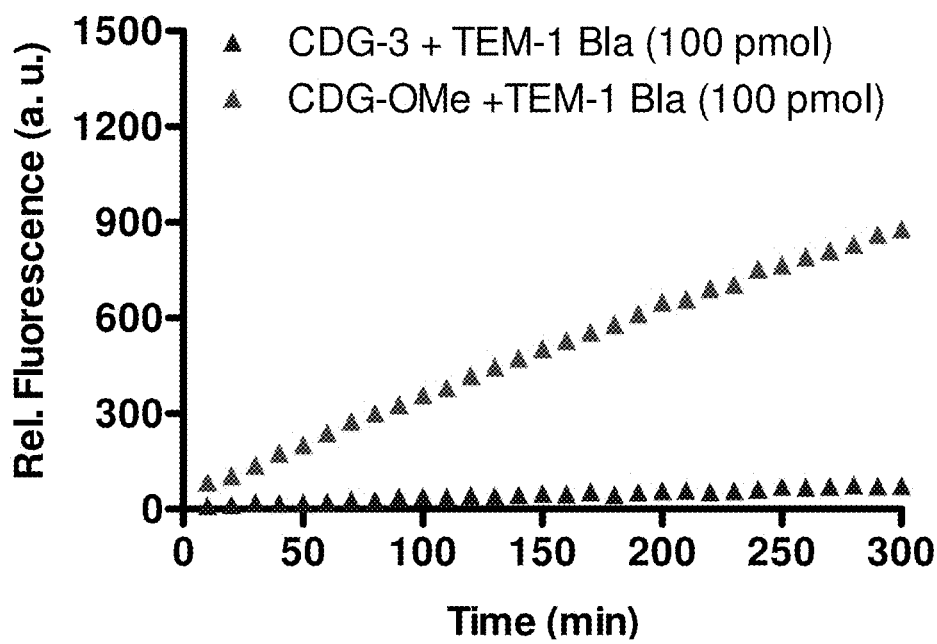
Figure 4C:
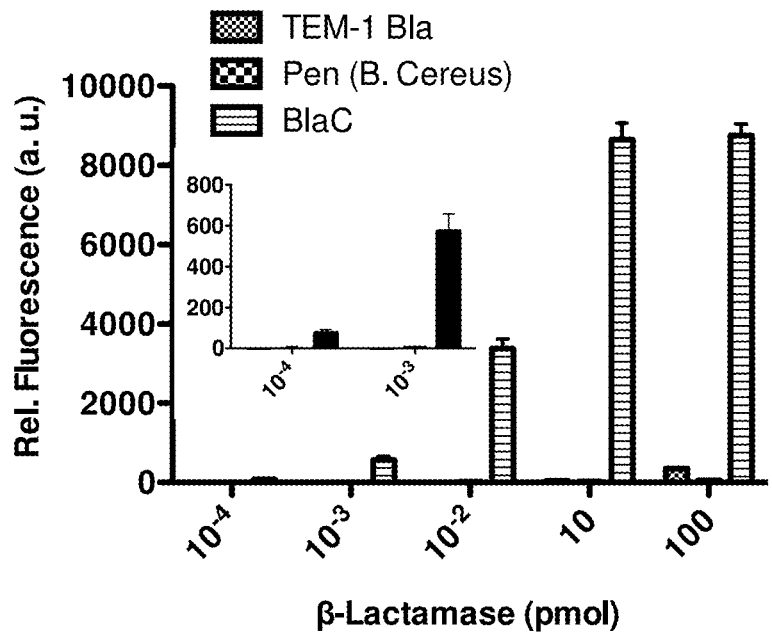
Figure 4D:
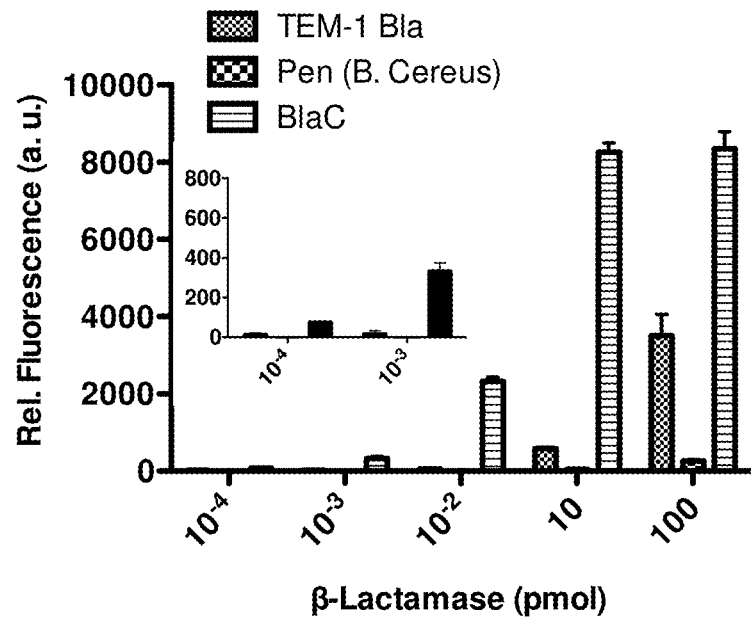

Fluorogenic probes with a longer emission wavelength generally improve sensitivity of bacteria detection by reducing background signal upon excitation. Therefore, the cyclopropyl substitution was introduced to the BlaC-specific green fluorogenic probe CDG-OMe producing CDG-3 (FIG. 3). FIG. 3 outlines the synthesis starting from readily available cephalosporin derivative 1. Mannich reaction of 1 with formaldehyde and dimethylamine hydrochloride gave the C-2 methylene cephem sulfoxide 2. After reduced by trifluoroacetic anhydride (TFAA) and sodium iodide, the obtained intermediate 3 was further subjected to TFAA and sodium iodide, diazomethane, and subsequently lithium chloride to provide the key intermediate 5. Tokyo green dye was introduced by a substitution reaction in the presence of potassium bicarbonate and 18-crown-6. Finally, the fluorogenic probe CDG-3 was obtained after a methoxylation reaction with tert-butyl hypochlorite and lithium methoxide, followed by deprotection with trifluoroacetic acid.

Figure 7:
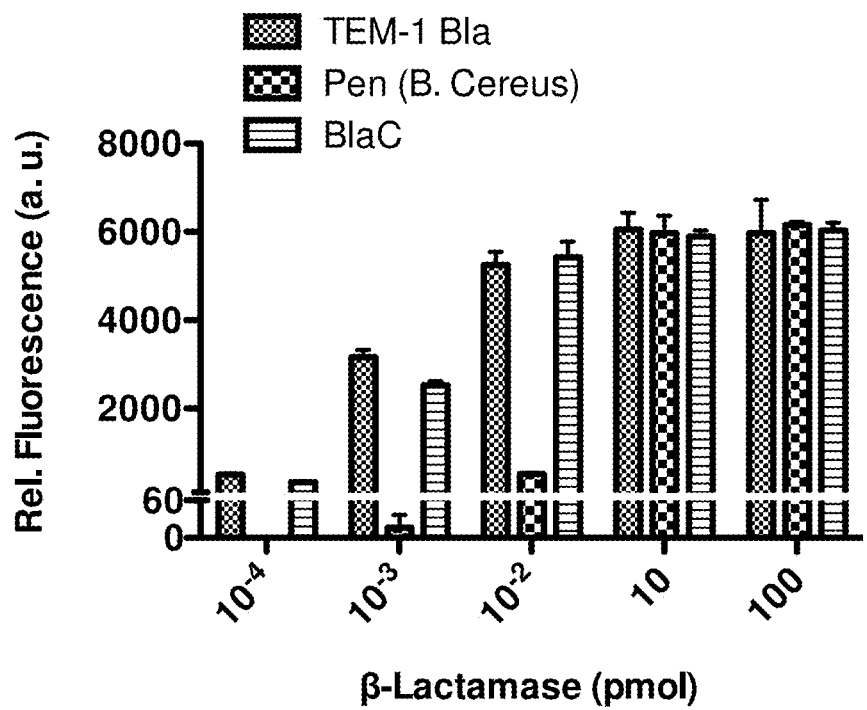
FIG. 7 shows fluorescence intensity of CDG-1 (10 μM) by serial dilutions of β-lactamases for 3 h. Data was collected in a 384-well plate with a total volume of 25 μL in each well. Fluorescence was measured with excitation at 490 nm and emission at 535 nm. Relative fluorescence represents the difference in fluorescence intensity with and without β-lactamase incubation. Error bars are ±SD.
Figure 8A:
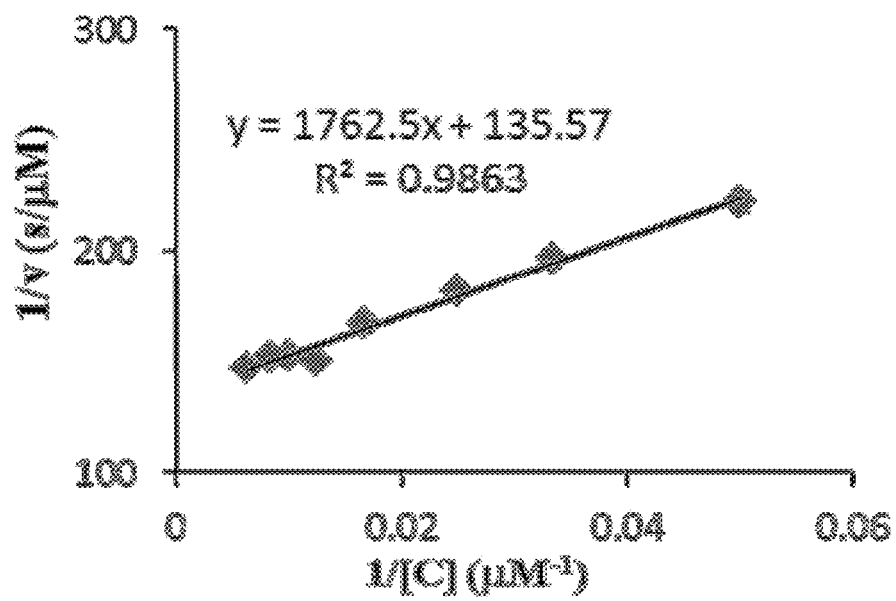
FIGS. 8A-8H compare Lineweaver-Burke plots of β-lactamases with CDC series probes in MES (100 mM with 0.1% surfactant, pH 6.6). BlaC with 2R-CDC-1 (8A); TEM-1 Bla with 2R-CDC-1 (8B); BlaC with 2S-CDC-1 (8C); TEM-1 Bla with 2S-CDC-1 (8D); BlaC with CDC-Cp (8E); TEM-1 Bla with CDC-Cp (8F); BlaC with CDC-OMe-Cp (8G); TEM-1 Bla with CDC-OMe-Cp (8H). Error bars indicate the standard deviations of three replicate experiments.
Figure 8B:
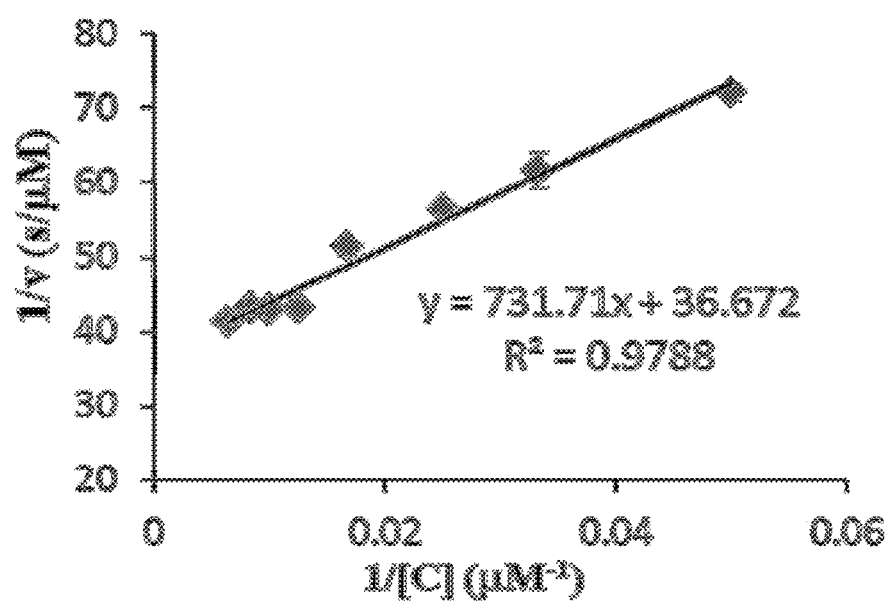
Figure 8C:
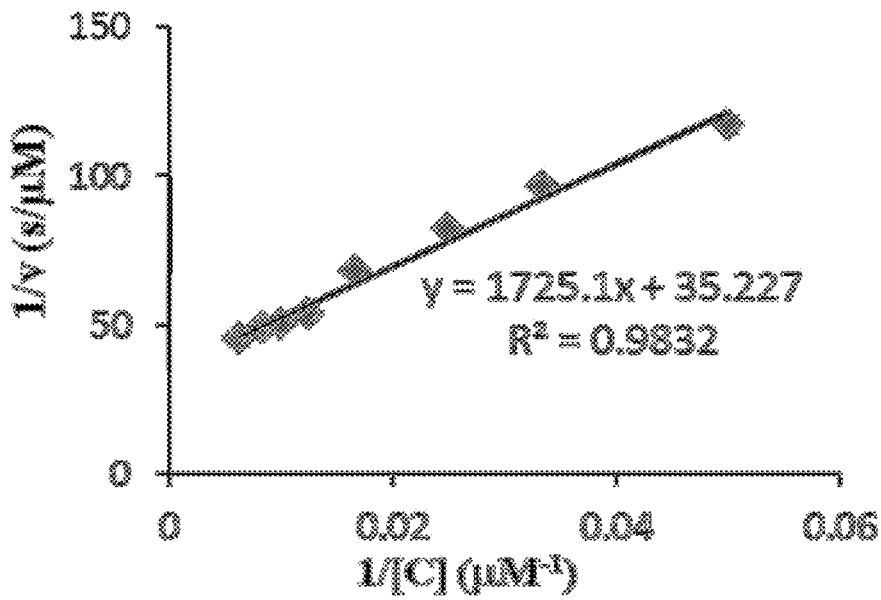
Figure 8D:
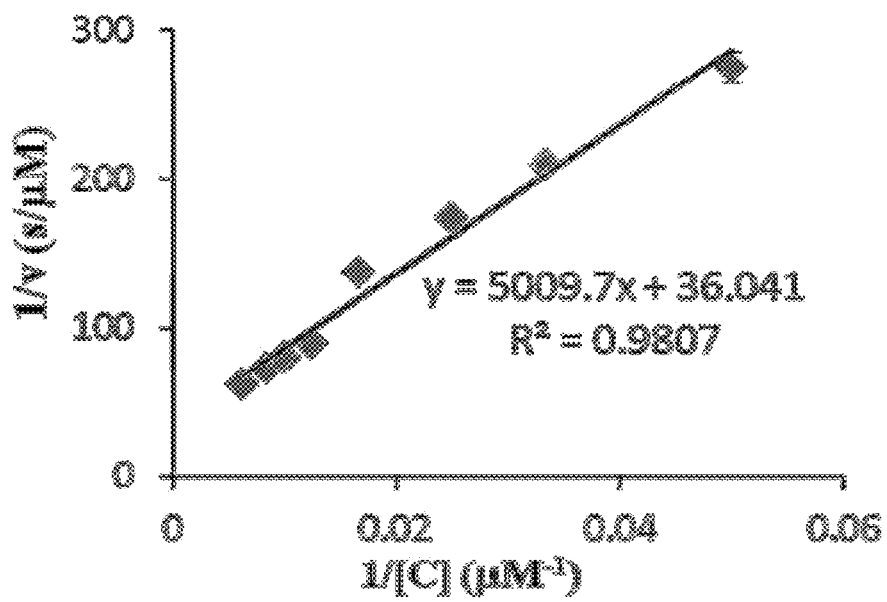
Figure 8E:
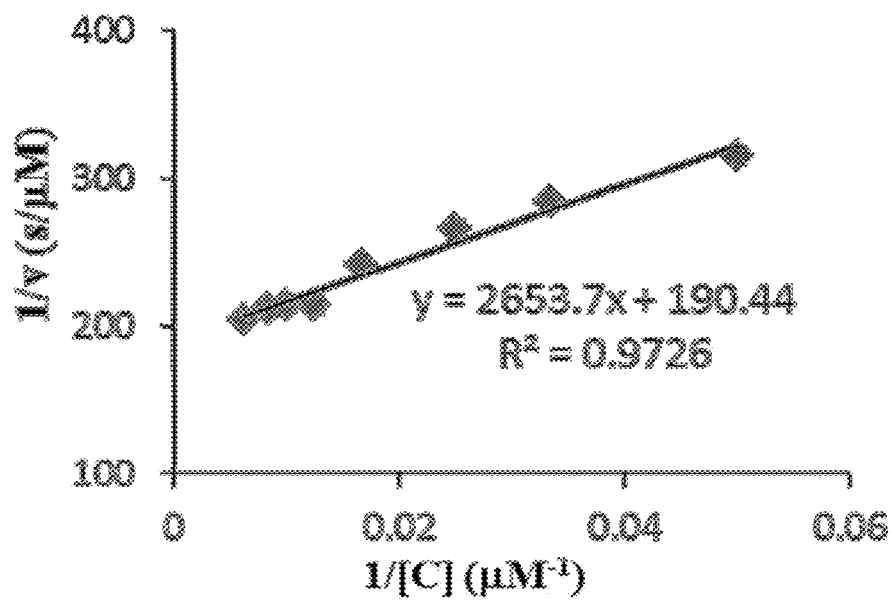
Figure 8F:
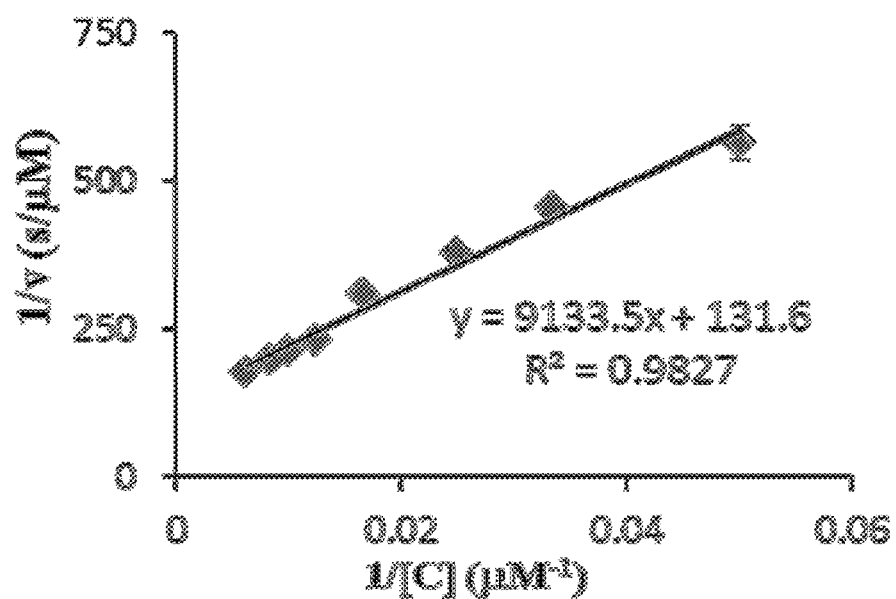
Figure 8G:
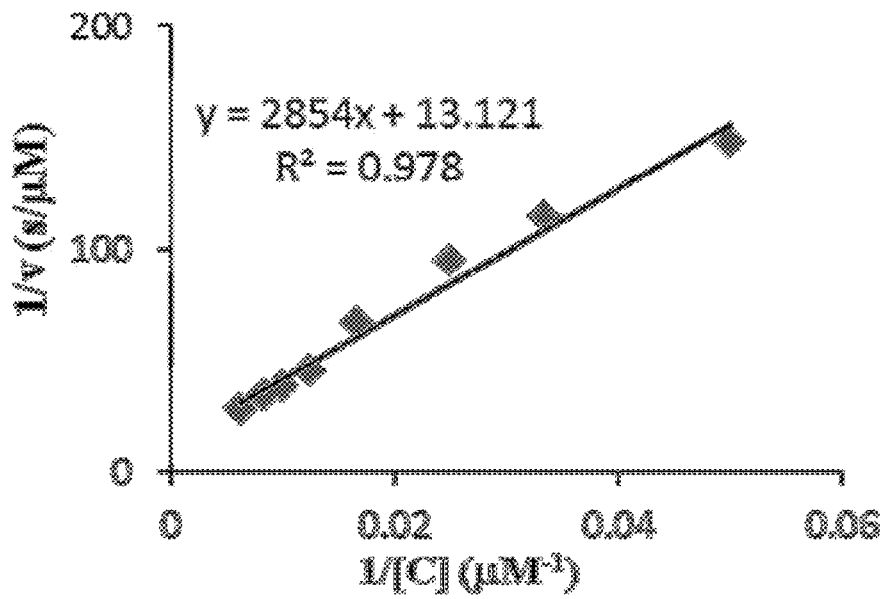
Figure 8H:
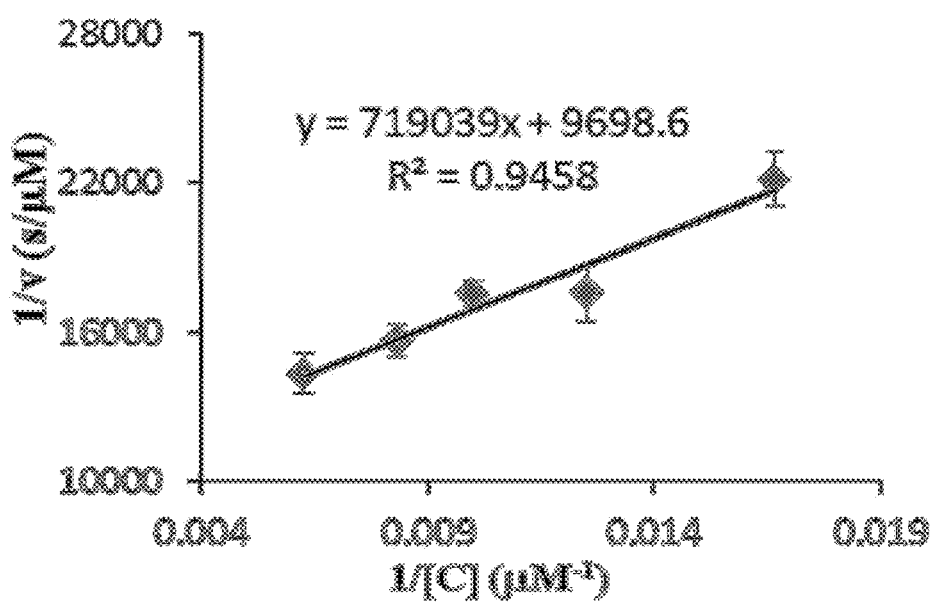
Figure 9A:
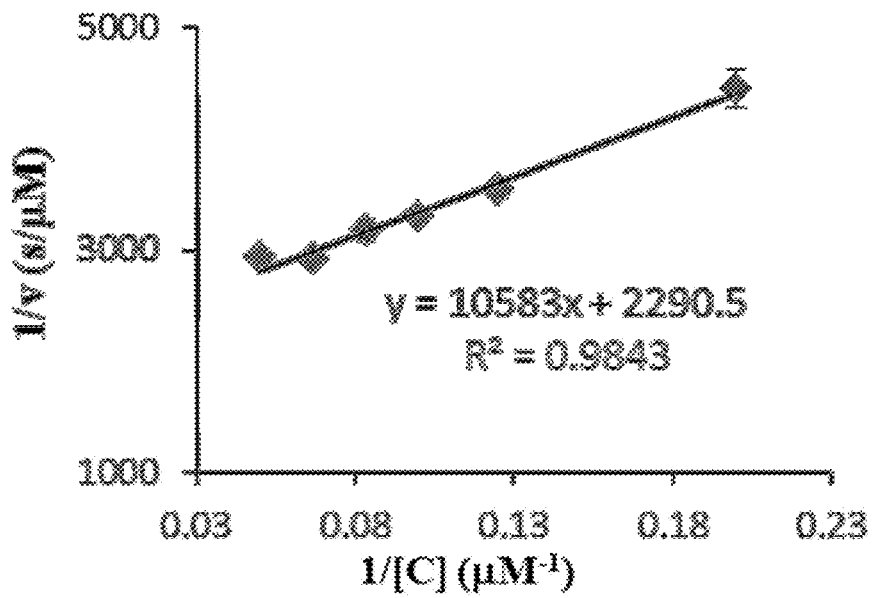
FIGS. 9A-9E compare Lineweaver-Burke plots of β-lactamases with CDG series probes in MES (100 mM with 0.1% surfactant, pH 6.6). BlaC with CDG-3 (9A); TEM-1 Bla with CDG-3 (9B); Pen with CDG-3 (9C); Pen with CDG-1 (9D); Pen with CDG-OMe (9E). Error bars indicate the standard deviations of three replicate experiments.
Figure 9B:
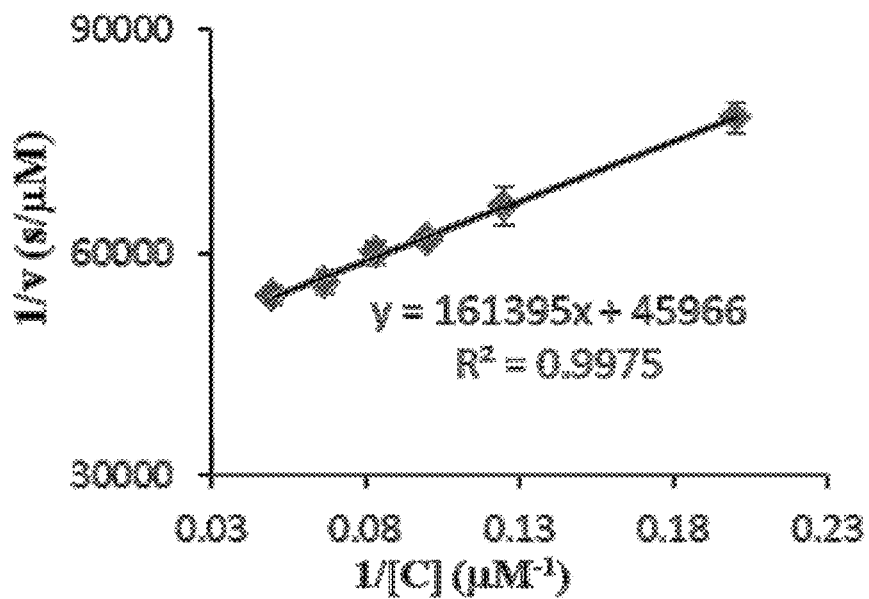
Figure 9C:
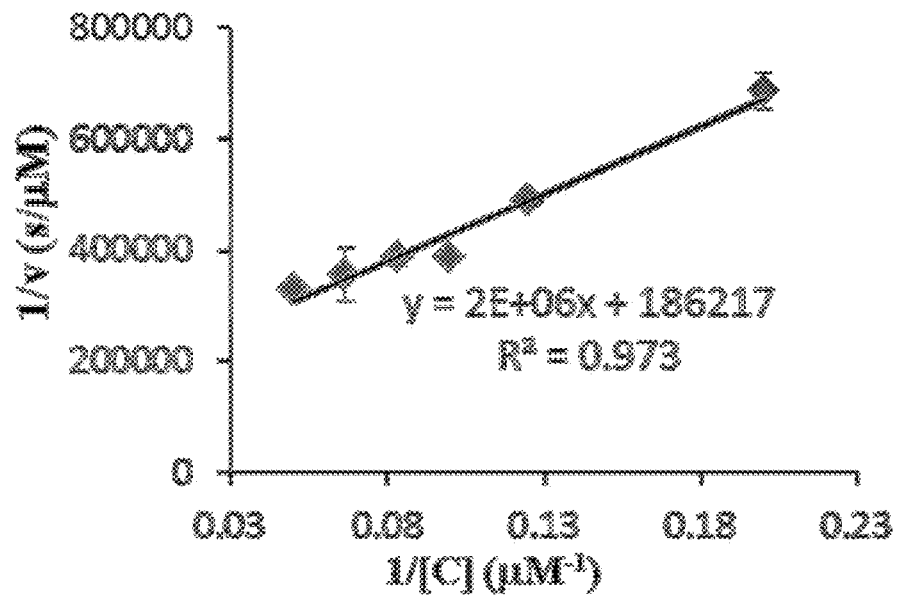
Figure 9D:
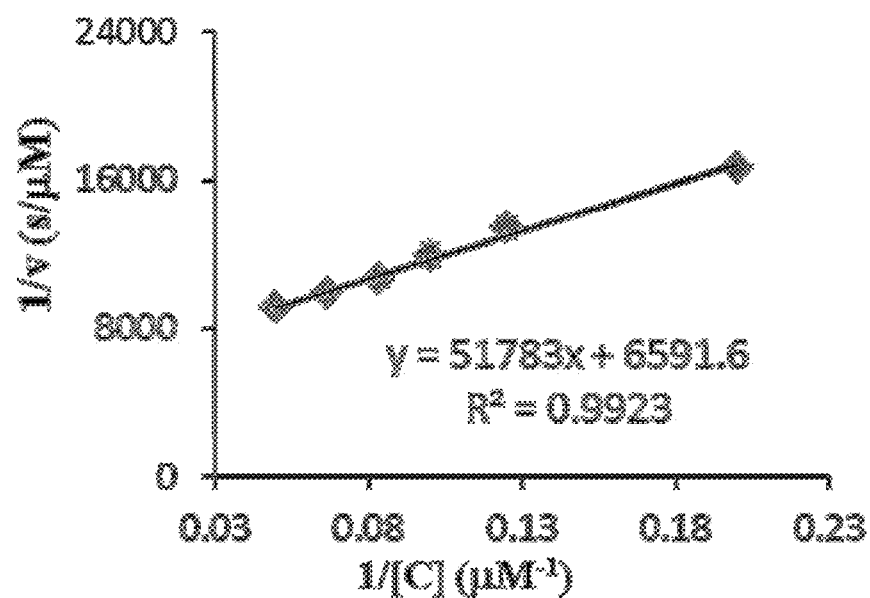
Figure 9E:
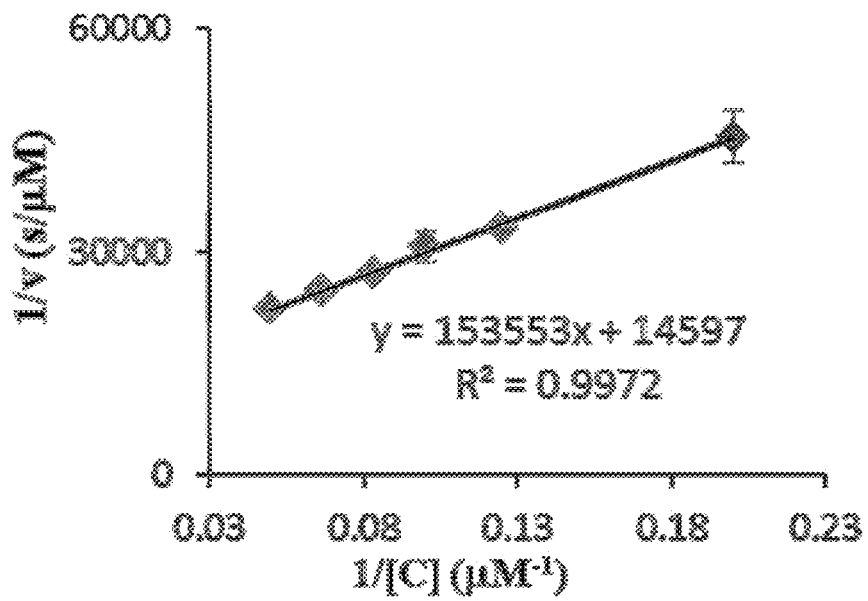
Figure 10A:
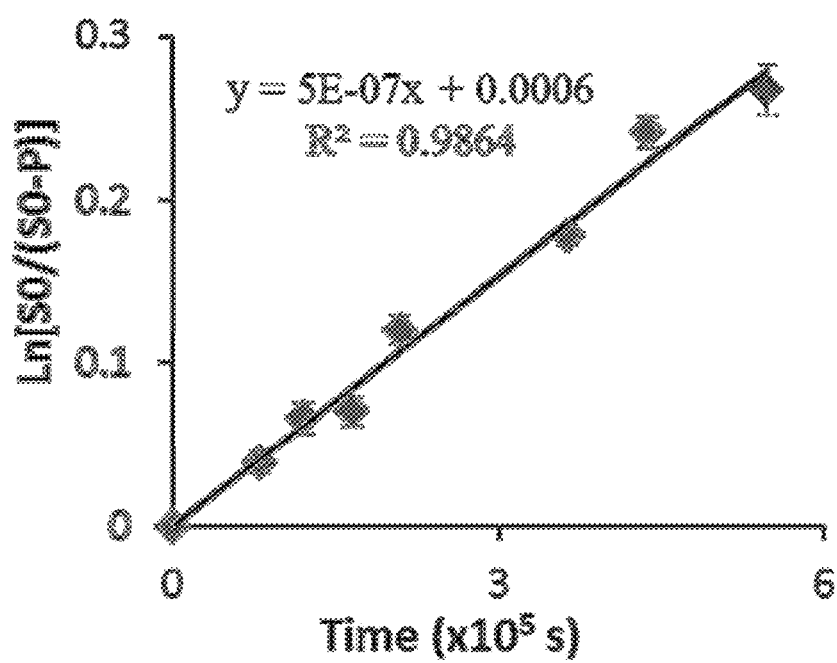
FIGS. 10A-10E compare stability of fluorogenic probes in MES (100 mM with 0.1% surfactant, pH 6.6) at room temperature (22° C.). 2R-CDC-1 (10A); 2S-CDC-1 (10B); CDC-OMe (10C); CDC-OMe-Cp (10D); CDG-3 (10E). Error bars indicate the standard deviations of three replicate experiments.
Figure 10B:
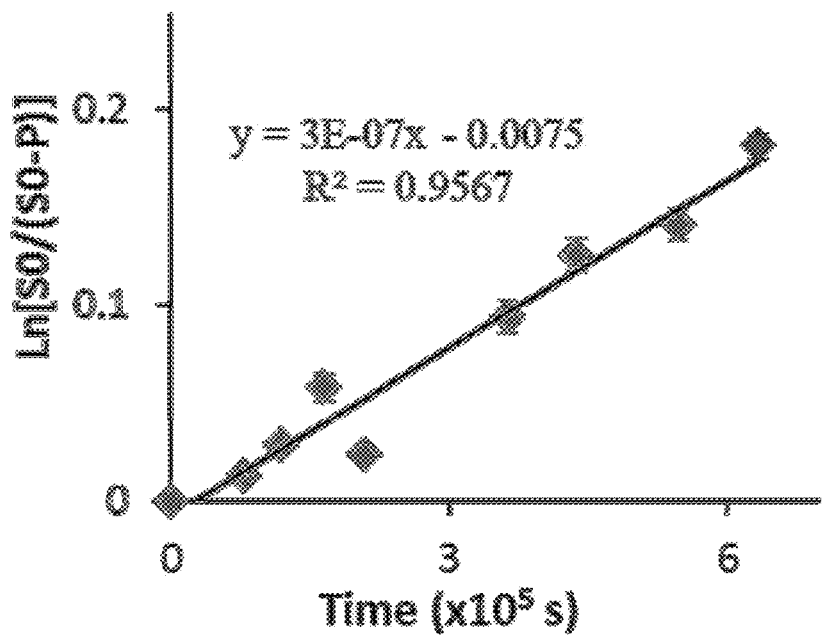
Figure 10C:
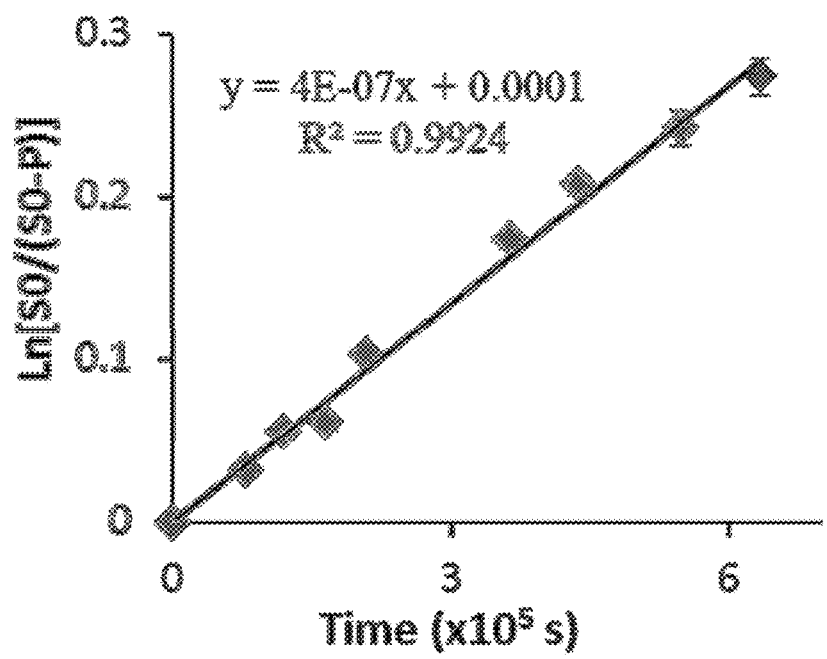
Figure 10D:
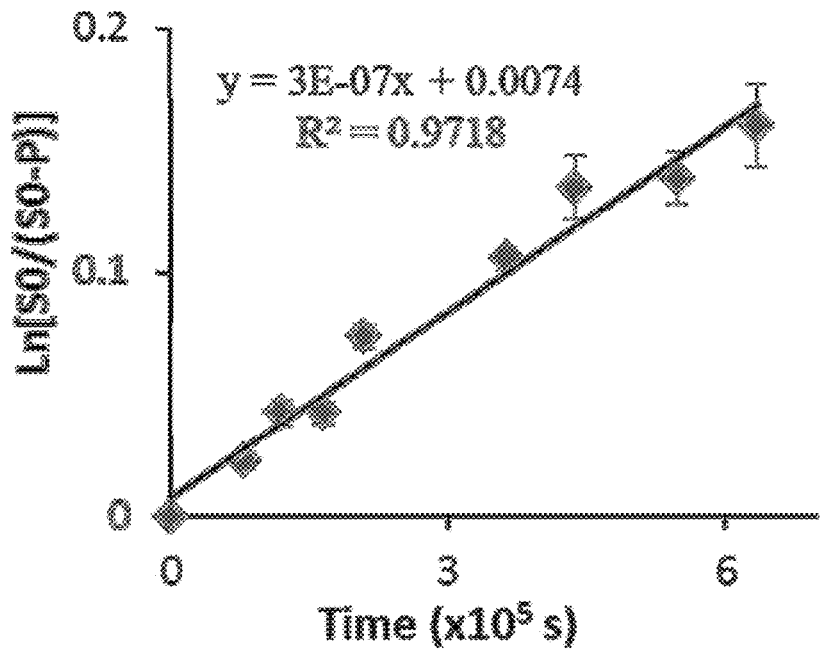
Figure 10E:
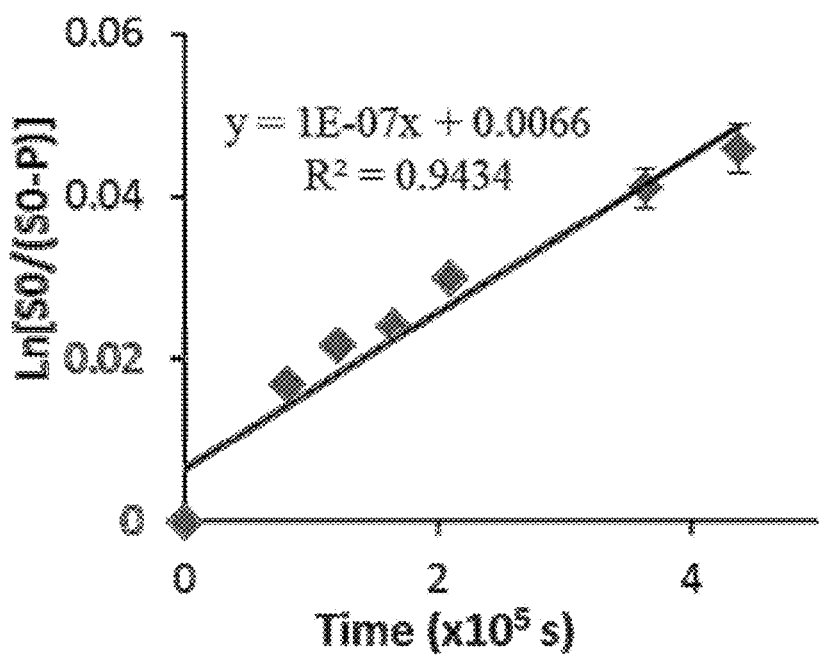

Similar to CDG-OMe, CDG-3 generated a 214-fold increase in fluorescence after complete hydrolysis by BlaC (FIG. 7). CDG-3 also showed better selectivity for BlaC over TEM-1 along with better sensitivity (Table 1, FIG. 2). As shown in FIGS. 4A-4D, CDG-3 generated higher fluorescent signal than CDG-OMe when incubated with the same amount of BlaC ($10^{-3}$ pmol, FIG. 4A), demonstrating its enhanced sensitivity. Furthermore, its increased specificity is demonstrated through its much slower hydrolysis by TEM-1 Bla than CDG-OMe (FIG. 4B), a 100,000-fold higher concentration of TEM-1 Bla than BlaC still produced less fluorescent signal than that of BlaC. CDG-3 also showed little activity towards penicillinase isolated from *Bacillus cereus* (Pen) (FIG. 4C), while some activity is shown with CDG-OMe in the presence of a large amount of Pen (100-100 pmol). Kinetic measurements confirmed the remarkable specificity of CDG-3 for BlaC: its catalytic efficiency ($2.4 \times 10^5$ s$^{-1}$M$^{-1}$) is 120,000 fold higher than for TEM-1 Bla (2 s$^{-1}$M$^{-1}$) and 800,000 fold higher than for Pen (0.3 s$^{-1}$M$^{-1}$). Finally, the stability of CDG-3 in buffer is also improved, evidenced from its lower spontaneous hydrolysis rate of $1.0 \times 10^{-7}$ s$^{-1}$ (MES buffer, 0.1 M, pH 6.6) than that of CDG-OMe ($1.9 \times 10^{-7}$ s$^{-1}$).

Figure 5A:
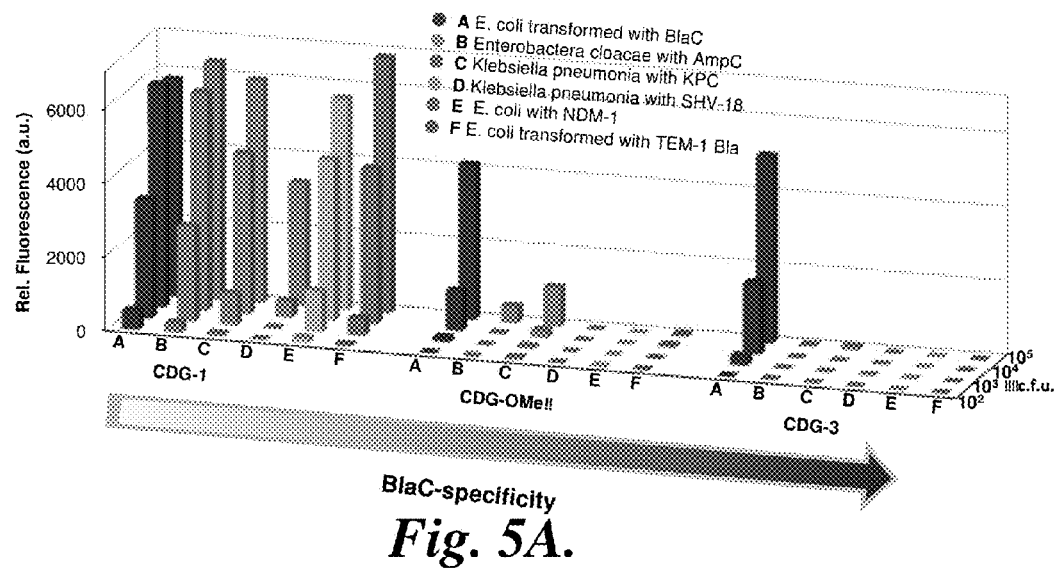
FIGS. 5A-5C compare β-lactamase specificity of CDG probes.
Figure 5B:
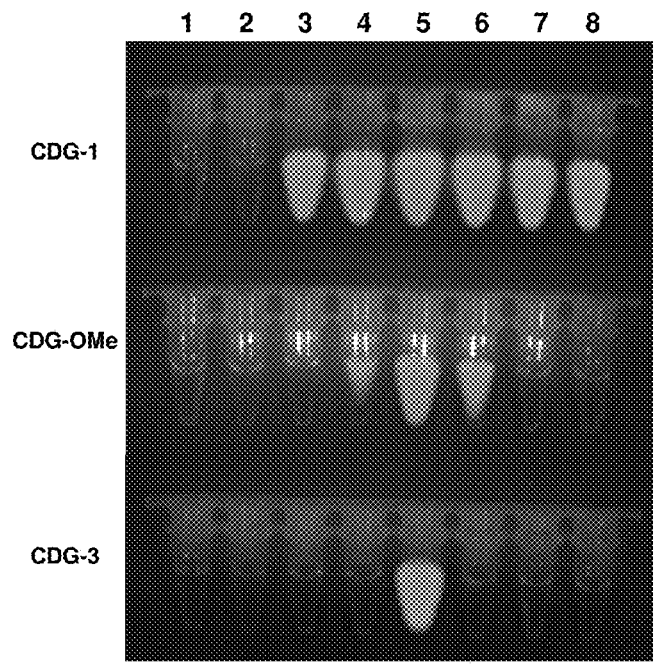

To further demonstrate the specificity of CDG-3 for BlaC, its activity was tested with a number of clinically prevalent strains with known high sensitivity to broad-spectrum cephalosporins, specifically, *K. pneumonia* with extended-spectrum β-lactamase (ESBL) SHV-18, *E. cloacae* with AmpC β-lactamase, *K. pneumoniae* with Class A carbapenemase KPC, and *E. coli* with class B metallo β-lactamase NDM-1. *E. coli* transformed with TEM-1 Bla was used as a negative control. Fluorescence enhancements of indicated probes (10 μM) were recorded after three hours of incubation across a series of diluted β-lactamase-expressing bacteria, and shown in FIG. 5A. As expected, non-specific probe CDG-1 showed fluorescent signal turn-on with all bacteria, and CDG-OMe showed much better selectivity for BlaC over other β-lactamase expressing bacteria. However, at $10^5$ colony forming unit (c.f.u.), both AmpC and KPC generated increased fluorescence emission with CDG-OMe: the fluorescent intensity ratio of AmpC to BlaC ($I_{AmpC}/I_{BlaC}$) was 1/9, and $I_{KPC}/I_{BlaC}=1/4$. On the other hand, CDG-3 showed further enhanced specificity as compared to CDG-OMe: in the presence of $10^5$ c.f.u., $I_{AmpC}/I_{BlaC}$ decreased to 1/130, and $I_{KPC}/I_{BlaC}$ dropped to 1/50. FIG. 5B shows the fluorescence images of $10^6$ c.f.u. β-lactamase-expressing bacteria incubated with CDG probes: CDG-3 showed a positive fluorescence signal only with BlaC, not other β-lactamase-expressing bacteria.

Figure 5C:
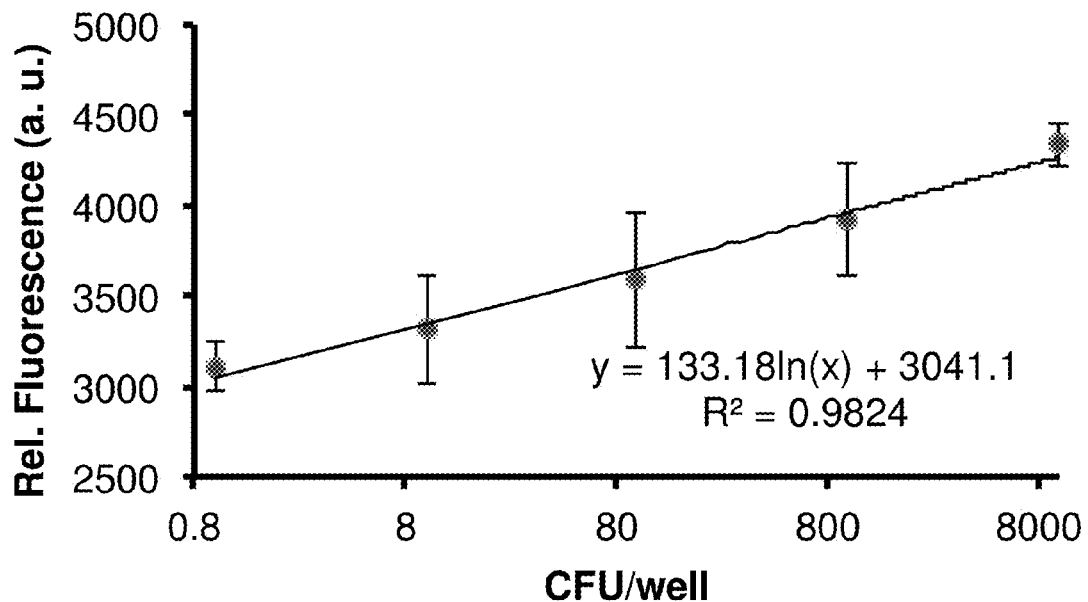
Figure 5D:
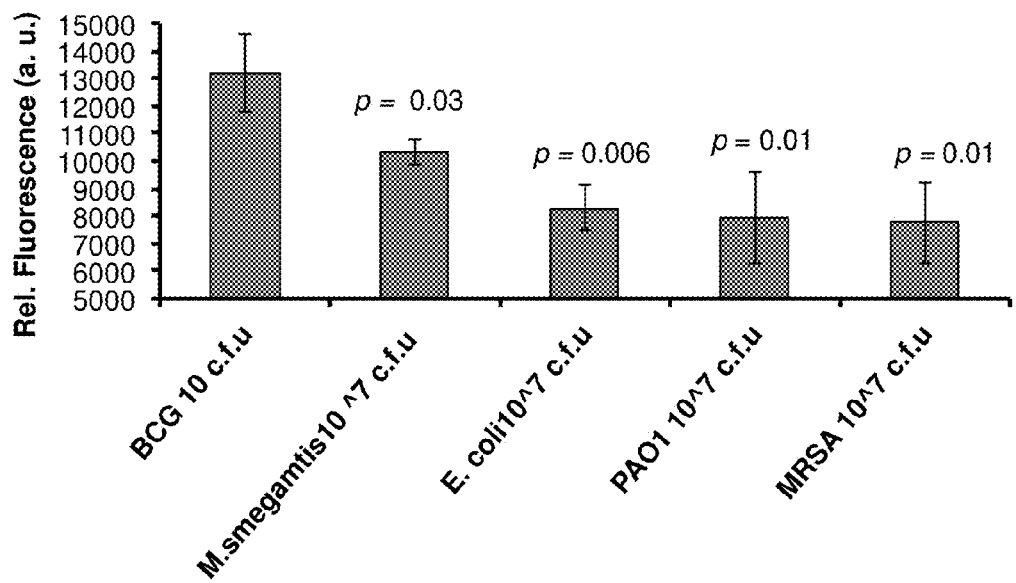
FIG. 5D illustrates specificity of CDG-3 for detecting BCG (10 c.f.u.) or indicated β-lactamase-expressing bacteria ($10^7$ c.f.u.) (H. X. Xie, J. Mire, Y. Kong, M. H. Chang, H. A. Hassounah, C. N. Thornton, J. C. Sacchettini, J. D. Cirillo, J. Rao, *Nat. Chem.* 2012, 4, 802-809) with the addition of antimicrobials used in mycobacterial selective medium (M. V. Rothlauf, G. L. Brown, R. C. Tilton. *J. Clin. Microbial.* 1981, 13, 76-79) for 0.3 bacterial generations (about 5-40 min). Data and error bars shown represent the means and standard deviations, respectively, of triplicate samples for all strains except BCG, which had six replicates. P values are comparisons versus BCG.

The suitability of CDG-3 for detecting the tuberculosis pathogen was evaluated in raw unprocessed pooled human sputum samples obtained from cystic fibrosis and chronic obstructive pulmonary disease patients (FIGS. 5C and 5D). BCG, an attenuated Mtb var. *bovis* strain, or other clinical prevalent bacteria that express β-lactamases, including *M. smegmatis, E. coli, P. aeruginosa* strain PA01, and methicillin-resistant *S. aureus* (MRSA), were incubated with CDG-3 in human sputum for 0.3 bacterial generations (about 5-40 min). Down to ten c.f.u. (P<0.05) BCG can be detected readily in sputum, and furthermore, fluorescence emission generated by 10 c.f.u. of BCG in sputum is significantly (P<0.05) higher than fluorescence from the negative controls and even from $10^7$ c.f.u. of *M. smegmatis, E. coli*, PA01, and MRSA.

In summary, 2-position substitution of the cephalosporin core structure on the substrate hydrolysis kinetics by β-lactamases was determined to provide a new family of fluorogenic probes with much higher sensitivity and specificity towards BlaC over previous generation BlaC probes for rapid detection of tuberculosis pathogen. Representative new probe CDG-3 has a cyclopropane ring substitution at the 2-position in addition to the methoxy substitution at the 7-position, and shows more than 120,000-fold and 800,000-fold selectivity for BlaC over TEM-1 Bla, and Penicillinase, respectively. The enhanced specificity enables live bacteria differentiation and the detection of tuberculosis pathogen in raw unprocessed human sputum samples. Furthermore, CDG-3 has additional advantages over previous probes because it avoids undesired 2,3-double bond isomerization of the cephalosporin structure, and has increased chemical stability in buffer. CDG-3 thus appears to be a superior fluorogenic probe enabling a rapid, specific, sensitive, and low-cost diagnostic tool for point-of-care TB detection. CDG-3 may also be applied for high throughput TB drug screening.

The following examples are provided for the purpose of illustrating, not limiting, the invention.

EXAMPLES

Example 1

Materials and Methods

Purified TEM-1 β-lactamase was customarily prepared by the Biologics Process Development, Inc. (San Diego, Calif.). Penicillinase from *Bacillus cereus* was purchased from Sigma-Aldrich (catalogue No. P0389). Recombinant Blac was expressed in *E. coli*. All chemicals were purchased from commercial sources. *K. pneumonia* with SHV-18, *E. cloacae* with AmpC, *K. pneumoniae* with KPC, and *E. coli* with NDM-1 were provided by Dr. Niaz Banaei from the Stanford Medical Center Microbiology Lab. Fluorescence spectra were obtained on a Fluoromax-3 spectrafluorometer (Jobin Yvon). Kinetic experiments were performed in a M1000 microplate reader (TECAN, research triangle park, NC). Analytical TLC was performed with 0.25 mm silica gel 60F plates with fluorescent indicator (254 nm). The $^{1}$H and $^{13}$C NMR spectra were taken on Varian 300 MHz or 400 MHz magnetic resonance spectrometers. Data for $^{1}$H NMR spectra are reported as follows: chemical shifts are reported as δ in units of parts per million (ppm) relative to chloroform-d (δ 7.26, s); multiplicities are reported as follows: s (singlet), d (doublet), t (triplet), q (quartet), dd (doublet of doublets), m (multiplet), or br (broadened); coupling constants are reported as a J value in Hertz (Hz); the number of protons (n) for a given resonance is indicated nH, and based on the spectral integration values. HPLC was performed on a Dionex HPLC System (Dionex Corporation) equipped with a GP50 gradient pump and an inline diode array UV-Vis detector. A reversed-phase C18 (Phenomenex, 5 μm, 10×250 mm or Dionex, 5 μm, 4.6×250 mm) column was used with a MeCN (B)/H$_2$O (A) gradient mobile phase containing 0.1% trifluoroacetic acid at a flow of 1 or 3 mL/min for the analysis.

Example 2

Detection of Mycobacteria in Sputum

Mtb var. *bovis* strain BCG was cultured in 7H9 medium with a 10% oleic acid albumin dextrose complex (OADC) and 0.25% Tween-80 until it reached the log phase (optical density at 600 nm (OD600) of 0.5-1). *E. coli*, MRSA, *P. aeruginosa* strain PA01 and *M. smegmatis* were cultured in Luria-Bertani medium until OD600=0.5-1. After measuring the bacterial OD600, 10$^7$ c.f.u. of each bacterial strain was added into Eppendorf tubes. Bacteria were centrifuged, the supernatant removed and resuspended into the same medium (7H9 medium with 10% OADC) to normalize the autofluorescence from different media. A series of tenfold dilutions of BCG and *M. smegmatis* (10$^7$ CFU), *E. coli* (10$^7$ CFU), *Pseudomonas aeruginosa* (PA01, 10$^7$ CFU), *Staphylococcus aureus* (MRSA, 10$^7$ CFU) were added to pooled human sputum obtained from cystic fibrosis and COPD patients. Sputa were diluted 1:1 in in 200 mM MES buffer pH 6 plus 2% DTT and incubated 0.03 generations (about 40 min for BCG, 5 min for *M. smegmatis*, *E. coli*, PA01 and MRSA) at room temperature. The substrate, CDG-3, was then added and samples read immediately and after 40 min at room temperature in a 96-well plate using a Mithras LB940 plate reader at 490 nm (ex) and 535 nm (em).

Example 3

Determination of Maximum Fluorescence Activation of CDG-3 by BlaC

Figure 6:
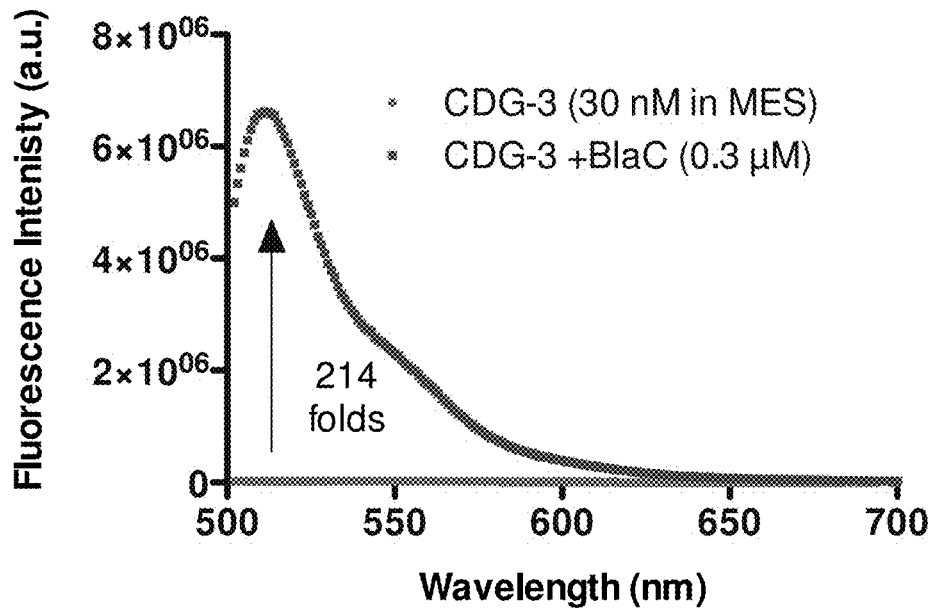
FIG. 6 compares fluorescent emission spectrum of CDG-3 (30 nM in MES buffer (0.1 M, pH=6.6, with 0.1% surfactant (3-[(3-cholamidopropyl)dimethylammonio]-1-propanesulfonate hydrate)) before and after treatment with BlaC (300 nM) for 30 min (excitation: 490 nm).

The results of the determination of maximum fluorescence activation of CDG-3 by BlaC are illustrated in FIG. 6.

Example 4

β-Lactamase Selectivity of CDG-1

The results of β-lactamse selectivity of CDG-1 are illustrated in FIG. 7.

Example 5

Enzymatic Kinetics and Stability Tests

Enzymatic kinetics and stability tests of new analogues were determined as described in Xie, H.; Mire, J.; Kong, Y.; Chang, M.; Hassounah, H. A.; Thornton, C. N.; Sacchettini, J. C.; Cirillo, J. D.; Rao, J. *Nat. Chem.* 2012, 4, 802. The results are illustrated in FIGS. 8-10.

Example 6

The Preparation and Characterization of 2R-CDC-1 and 2S-CDC-1

The preparation of 2R-CDC-1 and 2S-CDC-1 is illustrated schematically in FIG. 11 and described below.

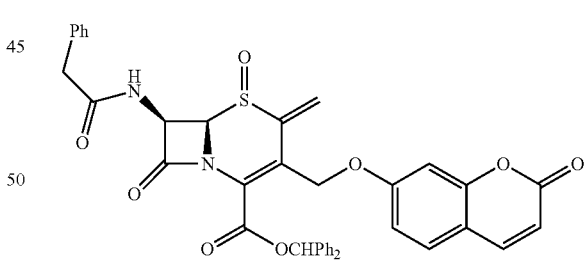

(1S,6R,7R)-Benzhydryl-2-methylene-3-(((2-oxo-2H-chromen-7-yl)oxy)methyl)-7-(2-phenylacetamido)-3-cephem-4-carboxylate 1-oxide (9)

To a solution of 8 (802 mg, 1.19 mmol) and formaldehyde (37% aqueous solution, 1 mL, 12.3 mmol) in DMF (7.5 mL) and dioxane (7.5 mL) was added dimethylamine hydrochloride (194 mg, 2.4 mmol) and the reaction mixture was heated to 55° C. for 6 h. After starting material disappeared (monitored by TLC), solvent and excess reagent were removed by Rota-Vap. Purification by flash chromatography on silica gel column afforded the titled compound 9 (661 mg, 84%). ¹H NMR (400 MHz, d⁶-DMSO) δ 8.67 (d, J=8.3 Hz, 1H), 7.99 (d, J=9.6 Hz, 1H), 7.57 (d, J=8.7 Hz, 1H), 7.42-7.11 (m, 15H), 6.98 (s, 1H), 6.88 (d, J=2.3 Hz, 1H), 6.80 (dd, J=8.6, 2.4 Hz, 1H), 6.41 (s, 1H), 6.31 (d, J=9.5 Hz, 1H), 6.24 (s, 1H), 6.00 (dd, J=8.3, 5.0 Hz, 1H), 5.15 (d, J=5.0 Hz, 1H), 5.11 (d, J=11.5 Hz, 1H), 4.87 (d, J=11.5 Hz, 1H), 3.69 (d, J=14.0 Hz, 1H), 3.57 (d, J=14.0 Hz, 1H); ¹³C NMR (101 MHz, d⁶-DMSO) δ 171.80, 164.51, 162.98, 161.54, 160.94, 160.64, 155.84, 144.98, 142.42, 140.11, 139.75, 136.44, 130.59, 130.04, 129.83, 129.15, 128.99, 128.56, 127.70, 127.60, 127.26, 127.05, 116.85, 113.46, 113.42, 102.06, 79.90, 69.74, 64.27, 59.47, 42.05, 36.46, 31.44; HRMS: Calculated for $C_{39}H_{30}N_2NaO_8S^+$ ([M+Na]⁺): 709.1615; Found: 709.1597.

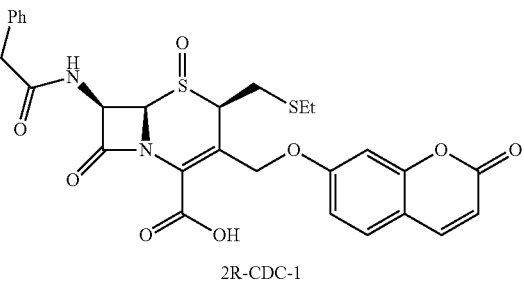

2R-CDC-1

(2R,6R,7R)-2-((ethylthio)methyl)-3-(((2-oxo-2H-chromen-7-yl)oxy)methyl)-7-(2-phenylacetamido)-3-cephem-4-carboxylic acid (2R-CDC-1)

To a mixture of 9 (68.9 mg, 0.1 mmol) and NaHCO₃ (4 mg, 0.05 mmol) in DMF (0.5 mL) was added ethanethiol (10 μL, 0.14 mmol) and the reaction was stirred at room temperature for 0.5 h. After starting material 9 disappeared, compound 10 as crude product was obtained after flash chromatography on a short silica gel column. Under Ar, trifluoroacetic anhydride (71 μL, 0.5 mmol) was added slowly to a mixture of sodium iodide (150 mg, 1 mmol) and compound 10 in acetone (anhydrous, 7 mL) at −40° C., the reaction mixture was then stirred at −20° C. for 1 h. After the disappearance of 10, reaction was cooled down to −78° C. and ethyl acetate was added, followed by sodium bicarbonate saturated aqueous solution. The reaction temperature was then warmed to room temperature. Organic layer was separated and the aqueous layer was extracted with ethyl acetate (20 mL×2). The combined organic layers were dried over MgSO₄. Crude compound 11 was then obtained after solvent was removed (the diastereomeric ratio was determined by ¹H NMR spectrum of the crude product to be 77.8:22.2), which was then subjected to a mixture CH₂Cl₂/TFA/TIPS (1/0.9/0.05 mL) at room temperature for 5 minutes. Pure 2R-CDC-1 (6 mg, 11% for 3 steps) and 2S-CDC-1 (25 mg, 44% for 3 steps) were obtained after HPLC purification on a C18 column. 2R-CDC-1: ¹H NMR (400 MHz, d⁶-DMSO) δ 9.15 (d, J=8.0 Hz, 1H), 7.99 (d, J=9.5 Hz, 1H), 7.64 (d, J=8.6 Hz, 1H), 7.35-7.15 (m, 5H), 6.98 (d, J=2.3 Hz, 1H), 6.94 (dd, J=8.6, 2.4 Hz, 1H), 6.30 (d, J=9.5 Hz, 1H), 5.62 (dd, J=8.0, 4.7 Hz, 1H), 5.23 (d, J=4.8 Hz, 1H), 5.09 (d, J=12.5 Hz, 1H), 4.94 (d, J=12.5 Hz, 1H), 4.30 (dd, J=9.1, 4.4 Hz, 1H), 3.56 (d, J=14.0 Hz, 1H), 3.51 (d, J=14.1 Hz, 1H), 3.26 (dd, J=13.7, 4.5 Hz, 1H), 2.79 (dd, J=13.6, 9.2 Hz, 1H), 2.54 (q, J=7.4 Hz, 2H), 1.13 (t, J=7.4 Hz, 3H); FIRMS: Calculated for $C_{28}H_{26}N_2NaO_7S^+$ ([M+Na]⁺): 589.1074; Found: 589.1057.

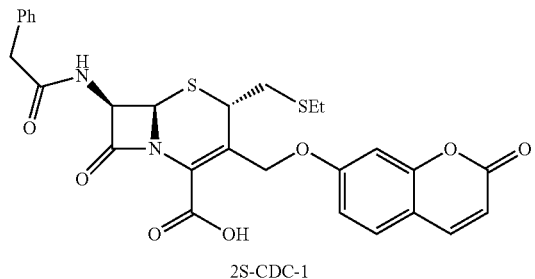

2S-CDC-1

(2S,6R,7R)-2-((ethylthio)methyl)-3-(((2-oxo-2H-chromen-7-yl)oxy)methyl)-7-(2-phenylacetamido)-3-cephem-4-carboxylic acid (2S-CDC-1)

¹H NMR (400 MHz, d⁶-DMSO) δ 9.19 (d, J=8.4 Hz, 1H), 7.99 (d, J=9.5 Hz, 1H), 7.64 (d, J=8.7 Hz, 1H), 7.35-7.16 (m, 5H), 7.06 (d, J=2.3 Hz, 1H), 6.98 (dd, J=8.6, 2.4 Hz, 1H), 6.30 (d, J=9.5 Hz, 1H), 5.76 (dd, J=8.3, 4.9 Hz, 1H), 5.26 (d, J=4.9 Hz, 1H), 5.00 (s, 2H), 3.86 (dd, J=10.1, 3.1 Hz, 1H), 3.54 (d, J=13.9 Hz, 1H), 3.48 (d, J=13.9 Hz, 1H), 3.13 (dd, J=14.1, 3.1 Hz, 1H), 2.83 (dd, J=14.1, 10.1 Hz, 1H), 2.53 (q, J=7.4 Hz, 2H), 1.10 (t, J=7.4 Hz, 3H); ¹³C NMR (101 MHz, d⁶-DMSO) δ 171.62, 165.30, 163.71, 161.79, 160.91, 155.95, 144.97, 136.38, 130.31, 129.71, 128.94, 128.28, 127.22, 122.78, 113.44, 102.08, 66.74, 60.19, 54.51, 42.24, 41.36, 36.92, 26.29, 15.43; HRMS: Calculated for $C_{28}H_{26}N_2NaO_7S^+$ ([M+Na]⁺): 589.1074; Found: 589.1062.

Example 7

The Preparation and Characterization of CDC-Cp and CDC-OMe-Cp

Figure 12:
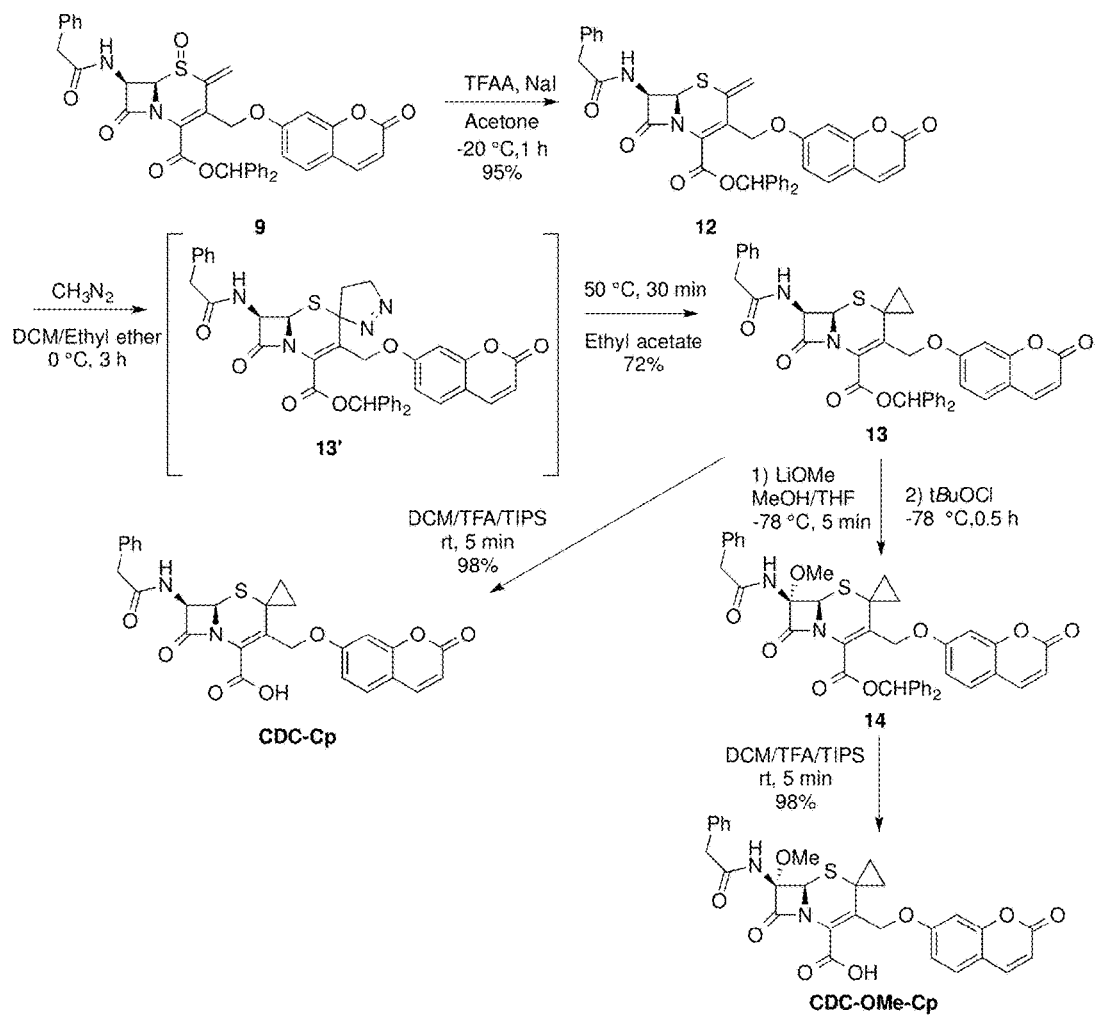
FIG. 12 is a schematic illustration of the synthesis of CDC-Cp and CDC-OMe-Cp.
Figure 13:
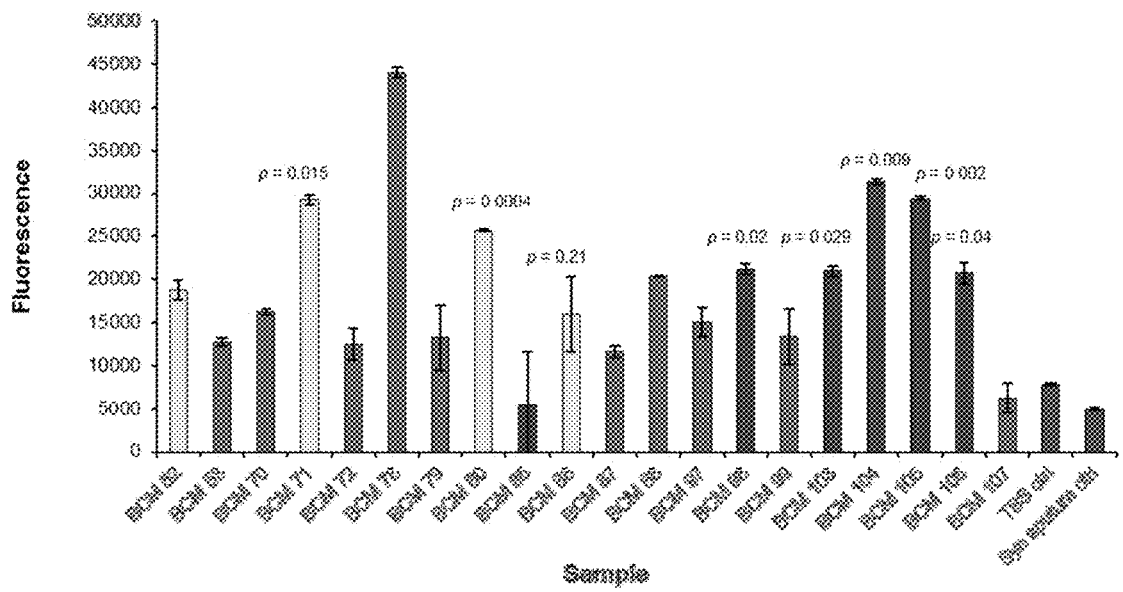
FIG. 13 illustrates clinical sample testing results using CDG3 as substrate. Twenty selected clinical samples (BCM52-107), chosen to contain approximately 50% tuberculosis (TB) positive samples, were tested in a blinded fashion using CDG3 in a reporter enzyme fluorescence (REF) assay after 1 h incubation at room temperature. Samples with fluorescence greater than twice that of the buffer (transport stabilization solution, TSS) control were considered positive (threshold shown by black horizontal line). Data and error bars shown represent the mean and standard deviation of top two values from a 100 position well scan for each sample. p-values are as compared to the TSS control.
Figure 14:
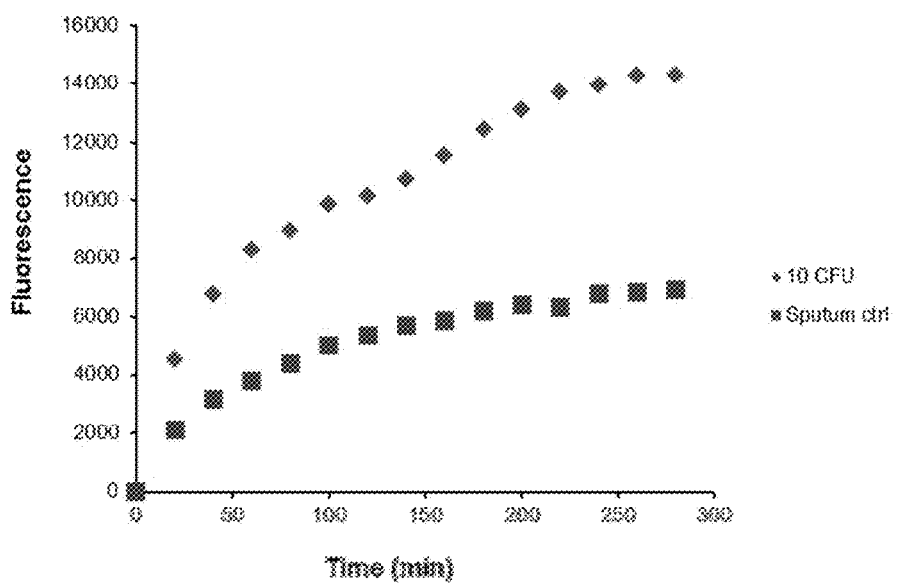
FIG. 14 compares fluorescence signal generated by 10 CFU BCG to TB-negative patient sputum control. 10 CFU BCG were incubated at room temperature in TB-negative patient sputum and processed. Detection was carried out using CDG3 in reporter enzyme fluorescence (REF) assay. The samples were read every 20 min at room temperature.
Figure 15:
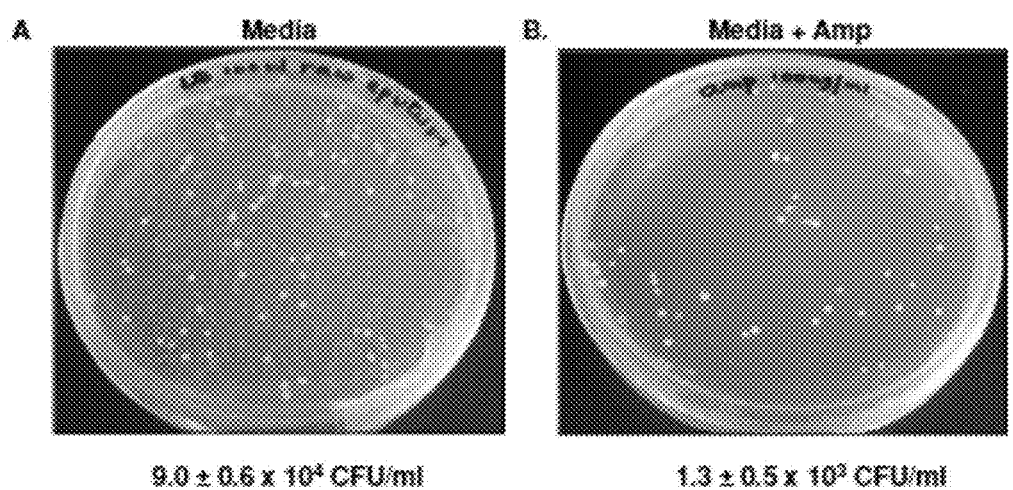
FIG. 15 illustrates bacterial abundance in TB-negative human sputum. Sputa from TB-negative patients were plated (A) on LB plates to determine bacterial abundance and (B) LB plates supplemented with 100 μg/ml ampicillin (Amp) to determine the abundance of β-lactamase producing bacteria. The samples were plated in duplicate and the average number of colony forming units (CFU/ml) and associated standard deviations shown below each plate.

The preparation of CDC-Cp and CDC-OMe-Cp is illustrated schematically in FIG. 12 and described below.

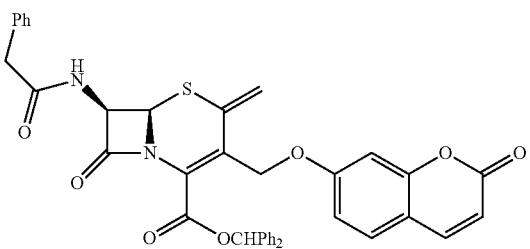

12

(6R,7R)-benzhydryl-2-methylene-3-(((2-oxo-2H-chromen-7-yl)oxy)methyl)-7-(2-phenylacetamido)-3-cephem-4-carboxylate (12)

Under Ar, trifluoroacetic anhydride (350 μL, 2.48 mmol) was added slowly to a mixture of sodium iodide (735 mg, 14.7 mmol) and compound 9 in acetone (anhydrous, 20 mL) at −40° C., the reaction mixture was then stirred at −20° C. for 1 h. The reaction was cooled down to −78° C. and ethyl acetate was added, followed by sodium bicarbonate saturated aqueous solution. The reaction was then warmed to room temperature. Organic layer was separated and the aqueous layer was extracted with ethyl acetate (20 mL×2).

The combined organic layers were dried over MgSO₄. Compound 12 (314 mg, 95%) was then obtained by flash chromatography purification. ¹H NMR (400 MHz, CDCl₃) δ 7.63 (d, J=9.5 Hz, 1H), 7.43-7.15 (m, 17H), 6.98 (s, 1H), 6.70 (dd, J=8.6, 2.4 Hz, 1H), 6.61 (d, J=2.3 Hz, 1H), 6.28 (d, J=9.5 Hz, 1H), 5.90 (dd, J=8.8, 4.8 Hz, 1H), 5.81 (s, 1H), 5.68 (s, 1H), 5.11 (d, J=4.8 Hz, 1H), 4.98 (d, J=10.8 Hz, 1H), 4.77 (d, J=10.8 Hz, 1H), 3.68 (d, J=16.1 Hz, 1H), 3.62 (d, J=16.1 Hz, 1H); ¹³C NMR (101 MHz, CDCl₃) δ 171.47, 163.71, 161.27, 161.23, 155.86, 143.53, 138.87, 138.66, 133.70, 130.69, 129.72, 129.52, 129.06, 128.75, 128.72, 128.65, 128.37, 128.09, 128.06, 127.10, 126.91, 123.38, 122.29, 113.79, 113.27, 113.01, 101.85, 80.21, 63.25, 60.54, 56.99, 43.49; HRMS: Calculated for $C_{39}H_{30}N_2NaO_7S^+$ ([M+Na]⁺): 693.1666; Found: 693.1658.

13

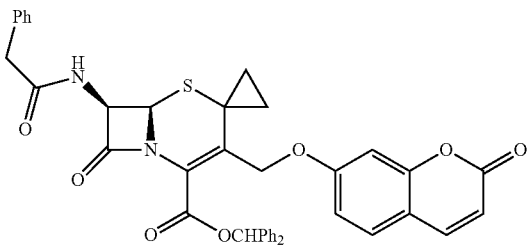

(6R,7R)-benzhydryl-3-(((2-oxo-2H-chromen-7-yl)oxy)methyl)-7-(2-phenylacetamido)-2-azaspiro[2,1'-cyclopropane]-3-cephem-4-carboxylate (13)

To a solution of 13 (314 mg, 0.47 mmol) in CH₂Cl₂ (20 mL) at 0° C. was added diazomethane (4.7 mmol) in ethyl ether (20 mL) and the reaction was kept at 0° C. for 3 h. After the reaction completed, acetic acid was added slowly at 0° C. to quench the excess diazomethane (until the reaction solution turned from yellow to colorless). The resulting mixture was washed with water and NaHCO₃ aqueous solution subsequently, and dried over MgSO₄. After filtration and Rota-Vap, the residue was dissolved in ethyl acetate and heated to 50° C. for 30 min until all intermediate 13' transformed (monitored by TLC). Purification by flash chromatography on silica gel column afforded the titled compound 13 (232 mg, 72%). ¹H NMR (400 MHz, CDCl₃) δ 7.62 (d, J=9.5 Hz, 1H), 7.42-7.14 (m, 17H), 6.96 (s, 1H), 6.66 (dd, J=8.6, 2.4 Hz, 1H), 6.52 (d, J=2.3 Hz, 1H), 6.28 (d, J=9.5 Hz, 1H), 6.10 (d, J=8.7 Hz, 1H), 5.92 (dd, J=8.8, 4.9 Hz, 1H), 5.22 (d, J=4.8 Hz, 1H), 4.37 (d, J=10.8 Hz, 1H), 4.29 (d, J=10.8 Hz, 1H), 3.66 (d, J=16.1 Hz, 1H), 3.60 (d, J=16.2 Hz, 1H), 1.52-1.40 (m, 2H), 1.34 (dd, J=9.3, 4.6 Hz, 1H), 1.03-0.95 (m, 1H); ¹³C NMR (101 MHz, CDCl₃) δ 165.06, 161.37, 161.19, 160.97, 155.83, 143.46, 139.08, 138.82, 133.70, 129.71, 129.52, 129.05, 128.69, 128.67, 128.57, 128.26, 128.10, 128.08, 127.10, 127.04, 113.85, 113.28, 112.82, 101.76, 79.82, 62.91, 60.09, 59.70, 43.53, 22.28, 21.29, 13.78; HRMS: Calculated for $C_{40}H_{32}N_2NaO_7S^+$ ([M+Na]⁺): 707.1822; Found: 707.1808.

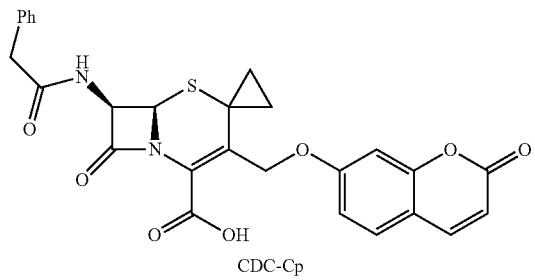 [SMILES: O=C(Cc1ccccc1)N[C@@H]1C(=O)N2C(C(=O)O)=C(COc3ccc4ccc(=O)oc4c3)C3(CC3)S[C@H]12]

CDC-Cp (6R,7R)-3-(((2-oxo-2H-chromen-7-yl)oxy)methyl)-7-(2-phenylacetamido)-2-azaspiro[2,1'-cyclopropane]-3-cephem-2-carboxylic acid (CDC-Cp)

Compound 13 (92 mg, 0.134 mmol) was subjected to a mixture of CH₂Cl₂/TFA/TIPS (1/0.9/0.05 mL) at room temperature for 5 minutes. After removing the solvent, the residue was then purified by flash chromatography on silica gel column to afford the titled compound CDC-Cp 68 mg, 98%). ¹H NMR (400 MHz, d⁶-DMSO) δ 9.16 (d, J=8.4 Hz, 1H), 7.98 (d, J=9.5 Hz, 1H), 7.62 (d, J=8.0 Hz, 1H), 7.40-7.16 (m, 5H), 7.00 (s, 1H), 6.94 (d, J=8.6 Hz, 1H), 6.29 (d, J=9.6 Hz, 1H), 5.79 (dd, J=7.5, 4.8 Hz, 1H), 5.28 (d, J=4.8 Hz, 1H), 4.60 (d, J=11.0 Hz, 1H), 4.41 (d, J=11.0 Hz, 1H), 3.53 (d, J=14.0 Hz, 1H), 3.47 (d, J=14.0 Hz, 1H), 1.52-1.40 (m, 2H), 1.39-1.29 (m, 1H), 0.99-0.90 (m, 1H); ¹³C NMR (101 MHz, d⁶-DMSO) δ 171.60, 165.64, 163.77, 161.70, 160.92, 155.97, 144.97, 136.39, 130.19, 129.99, 129.69, 128.93, 127.20, 124.98, 113.43, 113.33, 101.98, 63.67, 60.44, 59.69, 42.24, 21.81, 21.03, 13.41; HRMS: Calculated for $C_{27}H_{22}N_2NaO_7S^+$ ([M+Na]⁺): 541.1040; Found: 541.1033.

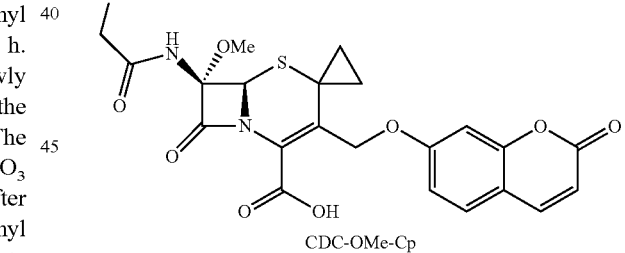

CDC-OMe-Cp (6R,7S)-7-methoxy-3-(((2-oxo-2H-chromen-7-yl)oxy)methyl)-7-(2-phenylacetamido)-2-azaspiro[2,1'-cyclopropane]-3-cephem-4-carboxylic acid (CDC-OMe-Cp)

Under the Ar, a solution of lithium methoxide (19.4 mg, 0.5 mmol) in methanol (anhydrous, 0.6 mL) was added dropwise to a solution of 13 (137 mg, 0.2 mmol) in anhydrous THF (3 mL) at −78° C. and the reaction was stirred for 5 min. Tert-butyl hypochlorite (36 μL, 0.32 mmol) was then added dropwise and the mixture was stirred at the same temperature for half an hour. Anhydrous THF (5 mL) was added to dilute and the resulting solution was poured in one port to an aqueous solution containing ammonium chloride and sodium bisulfate, extracted with ethyl acetate (15 mL×3) and dried over MgSO₄. Compound 14 was obtained as crude product after solvent was removed, which was then treated with a mixture $CH_2Cl_2$/TFA/TIPS (1/0.9/0.05 mL) at room temperature for 5 minutes. The titled compound CDC-OMe-Cp (45 mg, 39% for 2 steps) was obtained after HPLC purification. $^1$H NMR (400 MHz, d$^6$-DMSO) δ 9.56 (s, 1H), 7.97 (d, J=9.5 Hz, 1H), 7.61 (d, J=8.7 Hz, 1H), 7.37-7.15 (m, 5H), 7.01 (d, J=2.4 Hz, 1H), 6.93 (dd, J=8.6, 2.4 Hz, 1H), 6.28 (d, J=9.5 Hz, 1H), 5.31 (s, 1H), 4.54 (d, J=11.5 Hz, 1H), 4.39 (d, J=11.4 Hz, 1H), 3.59 (d, J=14.2 Hz, 2H), 3.54 (d, J=14.2 Hz, 2H), 3.35 (s, 3H), 1.52-1.42 (m, 1H), 1.41-1.31 (m, 1H), 1.29-1.18 (m, 1H), 1.00-0.87 (m, 1H); $^{13}$C NMR (101 MHz, d$^6$-DMSO) δ 172.42, 163.49, 161.65, 161.32, 160.92, 155.95, 144.96, 136.16, 130.19, 129.84, 129.61, 128.92, 127.22, 125.32, 113.42, 113.36, 101.97, 96.08, 64.58, 63.69, 53.17, 42.31, 21.86, 21.03, 18.54, 13.02; HRMS: Calculated for $C_{28}H_{24}N_2NaO_8S^+$ ([M+Na]$^+$): 571.1146; Found: 571.1125.

Example 8

The Preparation and Characterization of a Representative Fluorescent Probe: CDG-3

The preparation of a representative fluorescent probe of the invention, CDG-3, is illustrated schematically in FIG. 1 and described below.

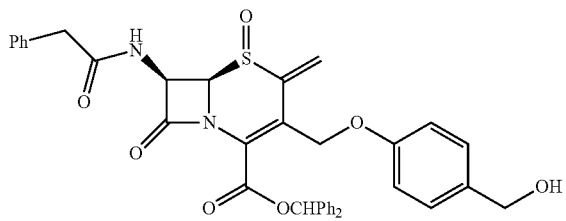

2

(1S,6R,7R)-benzhydryl-3-((4-(hydroxymethyl)phenoxy)methyl)-2-methylene-7-(2-phenylacetamido)-3-cephem-4-carboxylate-1-oxide (2)

To a solution of 1$^3$ (500 mg, 0.785 mmol) and formaldehyde (37% aqueous solution, 0.64 mL, 7.9 mmol) in DMF (6 mL) and dioxane (6 mL) was added dimethylamine hydrochloride (128 mg, 1.57 mmol) and the reaction mixture was heated to 55° C. for 6 h. Solvents and excess reagent were removed by Rota-Vap. Purification by flash chromatography on silica gel column afforded the titled compound 2 (418 mg, 82%). $^1$H NMR (400 MHz, d$^6$-DMSO) δ 8.64 (d, J=8.2 Hz, 1H), 7.46-7.21 (m, 14H), 7.17 (d, J=8.3 Hz, 2H), 6.99 (s, 1H), 6.76 (d, J=8.6 Hz, 2H), 6.36 (s, 1H), 6.22 (s, 1H), 5.98 (dd, J=8.3, 5.0 Hz, 1H), 5.13 (d, J=4.9 Hz, 1H), 5.07 (s, 1H), 5.02 (d, J=11.2 Hz, 1H), 4.74 (d, J=11.5 Hz, 1H), 4.40 (s, 2H), 3.68 (d, J=14.1 Hz, 1H), 3.56 (d, J=14.0 Hz, 1H); $^{13}$C NMR (101 MHz, d$^6$-DMSO) δ 171.79, 164.51, 160.71, 157.36, 142.63, 140.13, 139.88, 136.44, 135.99, 130.42, 129.82, 129.19, 129.12, 128.99, 128.70, 128.61, 128.50, 127.71, 127.25, 127.23, 127.13, 117.54, 114.99, 79.88, 69.68, 63.84, 63.14, 59.36, 42.04. HRMS: Calculated for $C_{37}H_{32}N_2NaO_7S^+$ ([M+Na]$^+$): 671.1822; Found: 671.1818.

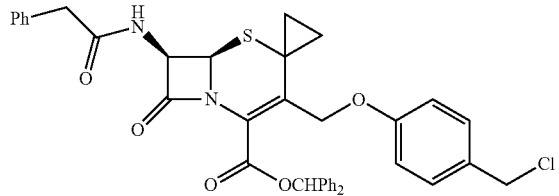

(6R,7R)-benzhydryl-3-((4-(chloromethyl)phenoxy)methyl)-7-(2-phenylacetamido)-2-azaspiro[2,1'-cyclopropane]-3-cephem-4-carboxylate (5)

Under Ar, trifluoroacetic anhydride (304 μL, 2.2 mmol) was added slowly to a mixture of sodium iodide (645 mg, 4.3 mmol) and 2 (275 mg, 0.43 mmol) in acetone (anhydrous, 10 mL) at −40° C., the reaction mixture was then stirred at −20° C. for 1 h. Reaction mixture was cooled down to −78° C. and ethyl acetate was added, followed by sodium bicarbonate saturated aqueous solution. The reaction temperature was then allowed to rise to room temperature. Organic layer was separated and the aqueous layer was extracted with ethyl acetate (20 mL×2). The combined organic layers were dried over $MgSO_4$ and the solvent was removed to afford 3. To a solution of 3 in $CH_2Cl_2$ (4 mL) at 0° C. was added fresh prepared diazomethane (4.9 mmol) in ethyl ether (10 mL) and the reaction was kept at 0° C. for 4 h. After the reaction completed, acetic acid (0.5 mL) was added slowly at 0° C. to quench excess diazomethane (until the reaction solution turned from yellow to colorless). The resulting mixture was washed with water and $NaHCO_3$ aqueous solution subsequently, and dried over $MgSO_4$. After filtration and Rota-Vap, the residue was dissolved in ethyl acetate (15 mL) and heated to 50° C. for 40 in. After solvent removal, the residue was purified by flash chromatography on silica gel column by using hexane/ethyl acetate (5/1-3/1) to afford the crude compound 4. To a solution of 4 obtained above, 2,6-lutidine (93 μL, 0.8 mmol) in DMF (anhydrous, 1.5 mL) at 0° C., was added slowly methanesulfonyl chloride (42 μL, 0.54 mmol). The reaction was stirred at 0° C. for 0.5 h and room temperature for 1 h. Lithium chloride (230 mg, 5.4 mmol) was then added and stirred at room temperature for another 2 h. Ethyl acetate and water were added. After separation, the aqueous layer was further extracted with ethyl acetate twice. The combined organic layer was washed with water and brine, and dried over $MgSO_4$. After solvents removal, the residue was then purified by flash chromatography on silica gel column by using hexane/ethyl acetate (3/1) as eluting solvents to afford the titled compound 5 (136 mg, 48% for 3 steps from 2). $^1$H NMR (400 MHz, CDCl$_3$) δ 7.45-7.11 (m, 17H), 6.99 (s, 1H), 6.65 (d, J=8.7 Hz, 2H), 6.24 (d, J=8.8 Hz, 1H), 5.91 (dd, J=8.8, 4.8 Hz, 1H), 5.21 (d, J=4.8 Hz, 1H), 4.55 (s, 2H), 4.37 (d, J=11.0 Hz, 1H), 4.32 (d, J=11.0 Hz, 1H), 3.64 (d, J=16.0 Hz, 1H), 3.59 (d, J=16.0 Hz, 1H), 1.60-1.43 (m, 2H), 1.36-1.25 (m, 1H), 1.00-0.89 (m, 1H); $^{13}$C NMR (101 MHz, CDCl$_3$) δ 171.48, 165.15, 161.60, 158.05, 139.25, 138.92, 133.85, 130.71, 130.36, 129.71, 129.46, 128.71, 128.65, 128.53, 128.25, 128.10, 128.00, 127.71, 127.20, 114.88, 79.75, 62.81, 60.07, 59.79, 46.37, 43.49, 22.50, 21.50, 13.80; HRMS: Calculated for $C_{38}H_{33}ClN_2NaO_5S^+$ ([M+Na]$^+$): 687.1691; Found: 687.1714.

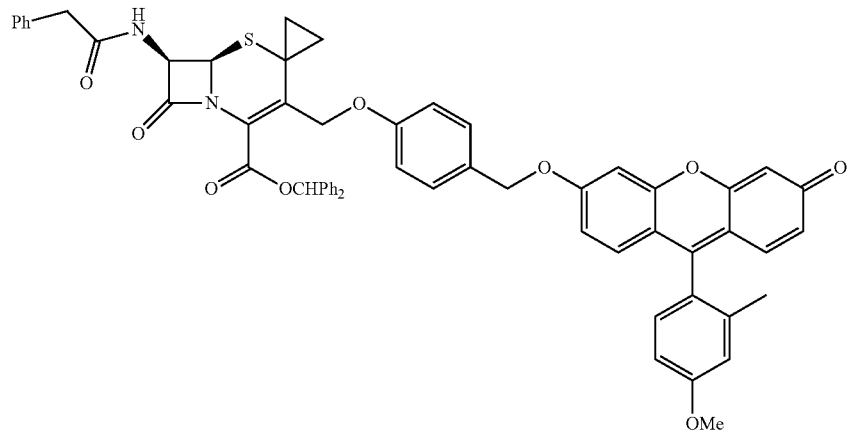

(6R,7R)-benzhydryl-3-((4-(((9-(4-methoxy-2-methylphenyl)-3-oxo-3H-xanthen-6-yl)oxy)methyl)phenoxy)methyl)-7-(2-phenylacetamido)-2-azaspiro[2,1'-cyclopropane]-4-carboxylate (6)

A mixture of Tokyo Green (56 mg, 0.17 mmol), potassium bicarbonate (34 mg, 0.34 mmol) and 18-crown-6 (30 mg, 0.11 mol) in DMF (anhydrous, 0.2 mL) were stirred at rt for 5 min, then 5 (73.6 mg, 0.11 mol) was added and the resulting mixture was stirred in dark at rt for 54 h. Purification by flash chromatography on silica gel column provided pure 6 (61.5 mg, 57%). $^1$H NMR (400 MHz, CDCl$_3$) δ 7.41-7.14 (m, 17H), 7.12-7.01 (m, 4H), 6.96 (s, 1H), 6.94-6.83 (m, 3H), 6.71 (d, J=8.7 Hz, 2H), 6.67 (dd, J=9.7, 1.9 Hz, 1H), 6.60 (s, 1H), 6.26 (d, J=8.8 Hz, 1H), 5.91 (dd, J=8.8, 4.9 Hz, 1H), 5.21 (d, J=4.8 Hz, 1H), 5.10 (s, 2H), 4.38 (d, J=11.1 Hz, 1H), 4.34 (d, J=11.0 Hz, 1H), 3.89 (s, 3H), 3.65 (d, J=16.1 Hz, 1H), 3.60 (d, J=16.0 Hz, 1H), 2.03 (s, 3H), 1.57-1.44 (m, 2H), 1.34-1.27 (m, 1H), 1.12-0.99 (m, 1H); $^{13}$C NMR (101 MHz, CDCl$_3$) δ 185.11, 171.45, 165.11, 164.04, 161.54, 160.73, 159.36, 158.26, 155.17, 139.26, 138.97, 138.05, 133.83, 131.22, 130.61, 130.07, 129.70, 129.64, 129.45, 128.67, 128.66, 128.44, 128.33, 128.17, 128.09, 127.98, 127.83, 127.18, 124.59, 118.83, 116.31, 115.31, 115.00, 114.83, 111.82, 105.72, 101.44, 79.72, 70.79, 62.80, 60.06, 59.79, 55.63, 43.48, 22.47, 21.51, 20.27, 13.82; FIRMS: Calculated for C$_{59}$H$_{49}$N$_2$O$_9$S$^+$ ([M+H]$^+$): 961.3153; Found: 961.3158.

(6R,7S)-7-methoxy-3-(((4-(((9-(4-methoxy-2-methylphenyl)-3-oxo-3H-xanthen-6-yl)oxy)methyl)phenoxy)methyl)-7-(2-phenylacetamido)-2-azaspiro[2,1'-cyclopropane]-4-carboxylic acid (CDG-3)

Under the Ar, a solution of lithium methoxide (10 mg, 0.26 mmol) in methanol (anhydrous, 0.3 mL) was added dropwise to a solution of 6 (62 mg, 0.065 mmol) in anhydrous THF (1 mL) at −78° C. and the reaction was stirred for 5 min. Tert-butyl hypochlorite (15 μL, 0.13 mmol) was then added dropwise and the mixture was stirred at the same temperature for half an hour. Anhydrous THF (5 mL) was added to dilute and the resulting solution was poured in one port to an aqueous solution containing ammonium chloride and sodium bisulfate, extracted with ethyl acetate (15 mL×3) and dried over MgSO$_4$. Compound 7 was obtained as crude product after solvent was removed, which was then treated with a mixture CH$_2$Cl$_2$/TFA/TIPS (3.8/0.2/0.05 mL) at ° C. for 3 h. The titled compound CDG-3 (35.5 mg, 67% for 2 steps) was obtained after HPLC purification. $^1$H NMR (400 MHz, d$^6$-DMSO) δ 9.55 (s, 1H), 7.46 (s, 1H), 7.41 (d, J=8.5 Hz, 2H), 7.37-6.92 (m, 14H), 6.68 (d, J=9.6 Hz, 1H), 6.57 (s, 1H), 5.29 (s, 1H), 5.25 (s, 2H), 4.44 (d, J=11.3 Hz, 1H), 4.33 (d, J=11.3 Hz, 1H), 3.84 (s, 3H), 3.59 (d, J=14.1 Hz, 1H), 3.54 (d, J=14.1 Hz, 1H), 3.35 (s, 3H), 1.98 (s, 3H), 1.49-1.43 (m, 1H), 1.39-1.33 (m, 1H), 1.26-1.20 (m, 1H), 0.94-0.89 (m, 1H); $^{13}$C NMR (101 MHz, d$^6$-DMSO) δ 180.84, 172.41, 165.79, 163.58, 161.32, 160.94, 159.56,

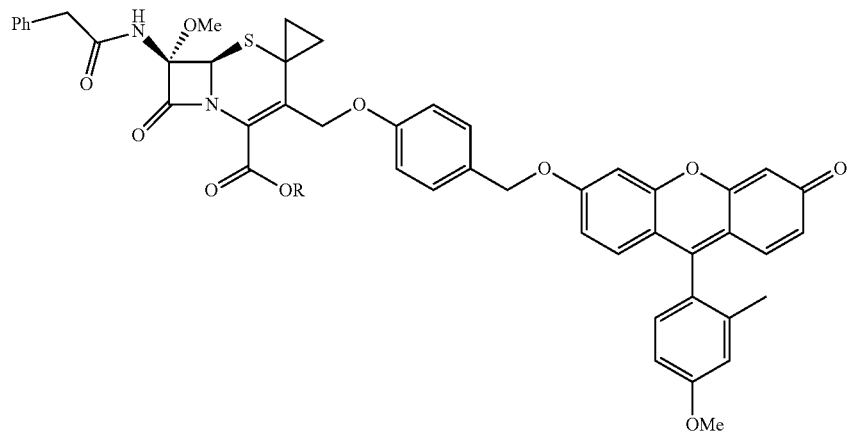

CDG-3

158.70, 156.26, 138.17, 136.17, 132.36, 131.28, 131.04, 130.69, 129.84, 129.26, 128.92, 128.77, 127.22, 126.87, 125.86, 124.41, 118.39, 116.87, 116.57, 115.92, 115.22, 112.49, 104.54, 102.06, 96.04, 71.12, 64.66, 63.11, 55.97, 53.15, 42.31, 21.12, 20.22; HRMS: Calculated for $C_{47}H_{41}N_2O_{10}S^+$ ($[M+H]^+$): 825.2476; Found: 825.2469.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound having the formula:

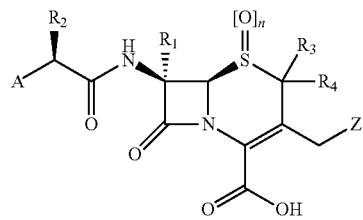

or an ester or a salt thereof,
wherein
A is C6-C10 aryl;
$R_1$ is selected from the group consisting of:
  (a) hydrogen,
  (b) methoxy, and
  (c) ethoxy;
$R_2$ is selected from the group consisting of hydrogen, C1-C3 alkyl, C1-C3 alkyl substituted with one or more halogens, and substituted piperazine;
$R_3$ and $R_4$ are independently selected from the group consisting of hydrogen, methyl, ethyl, propyl, halomethyl, haloethyl, halopropyl, or $R_3$ and $R_4$ taken together with the carbon atom to which they are attached form a cyclopropyl or a cyclobutyl ring, provided that $R_3$ and $R_4$ are not both hydrogen;
n is 0 or 1; and
Z is a moiety that provides a fluorescent, luminescent, or colorimetric signal when released from the compound.

2. A compound of claim 1 having the formula:

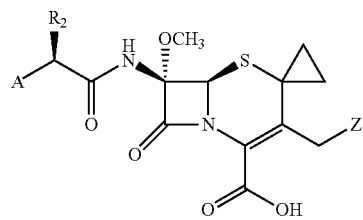

or an ester or a salt thereof.

3. A compound of claim 1 having the formula:

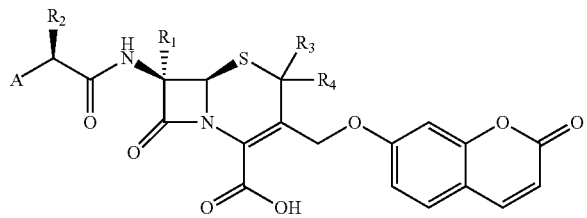

or an ester or a salt thereof.
4. The compound of claim 1, wherein A is phenyl.
5. The compound of claim 1, wherein $R_1$ is methoxy.
6. The compound of claim 1, wherein $R_2$ is hydrogen.
7. The compound of claim 1, wherein $R_3$ and $R_4$ taken together with the carbon atom to which they are attached form a cyclopropyl ring.
8. The compound of claim 1, wherein Z is a moiety that provides a fluorescent, luminescent, or colorimetric signal when released from the compound.
9. The compound of claim 1, wherein Z is

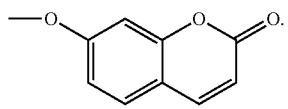

10. The compound of claim 1, wherein Z is

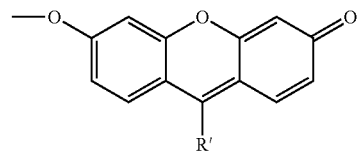

wherein R' is hydrogen or aryl.
11. The compound of claim 1, wherein Z is

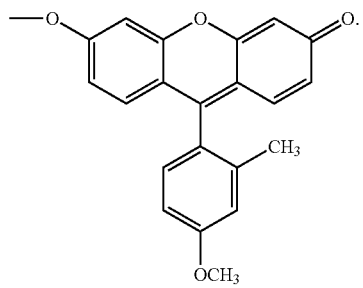 [SMILES: COc1ccc(-c2c3ccc(=O)cc-3oc3cc(OC)ccc23)c(C)c1]

12. A method for detecting β-lactamase in a sample, comprising:
  (a) contacting a sample with a compound of claim 1; and
  (b) measuring an optical signal generated from contacting the sample with the compound.
13. A method for diagnosing tuberculosis, comprising:
  (a) contacting a sample with a compound of claim 1; and
  (b) measuring an optical signal generated from contacting the sample with the compound.
14. The method of claim 13, wherein the sample is sputum, pleural fluid, spinal fluid, blood, urine, saliva, stool, tissue biopsies, tissue homogenates, directly in live animals or human patients, or a sample obtained by swabbing an area of interest on a subject.

15. The method of claim 13, wherein the sample comprises a pathogenic bacterial species selected from *Bacteroides, Clostridium, Streptococcus, Staphylococcus, Pseudomonas, Haemophilus, Legionella, Mycobacterium, Escherichia, Salmonella, Shigella*, or *Listeria*.

16. The method of claim 13, wherein measuring an optical signal comprises measuring fluorescence emission intensity.

17. An assay method for determining drug susceptibility of pathogenic bacteria in a subject infected by said pathogenic bacteria, comprising:
    (a) obtaining a biological sample from the subject;
    (b) contacting said biological sample with a drug effective against the pathogenic bacteria;
    (c) contacting said biological sample with a substrate for a β-lactamase of the pathogenic bacteria, wherein the substrate is a compound of claim 1;
    (d) delivering an excitation wavelength to the biological sample; and
    (e) measuring levels of a signal intensity at an emission wavelength produced by the product of the β-lactamase action on the substrate in the biological sample over a period of time; wherein no increase or a decrease in signal intensity levels over the time period correlates to susceptibility of the pathogenic bacteria to the drug.

18. An in vitro method for determining drug susceptibility of a pathogenic Mycobacteria in a subject infected by the same, comprising the steps of:
    (a) obtaining a biological sample from the subject;
    (b) contacting said biological sample with an anti-mycobacterial drug;
    (c) contacting said biological sample with a fluorogenic substrate for Mycobacterial β-lactamase, wherein the substrate is a compound of claim 1;
    (d) delivering an excitation wavelength to the biological sample; and
    (e) measuring levels of fluorescence at an emission wavelength produced by a fluorescent product of the β-lactamase action on the substrate in the biological sample over a period of time; wherein no increase or a decrease in fluorescence over the time period correlates to susceptibility of the pathogenic bacteria to the drug.

19. An assay system for monitoring drug susceptibility of pathogenic bacteria, comprising:
    (a) one or more color-producing substrates for a β-lactamase of the pathogenic bacteria, wherein the substrate is a compound of claim 1;
    (b) an assay device for visibly detecting a product of β-lactamase activity on the substrate; and
    (c) a reader configured to quantify visible signals emitted by the detected product.

* * * * *